(12) United States Patent
Leung et al.

(10) Patent No.: US 6,187,287 B1
(45) Date of Patent: *Feb. 13, 2001

(54) IMMUNOCONJUGATES AND HUMANIZED ANTIBODIES SPECIFIC FOR B-CELL LYMPHOMA AND LEUKEMIA CELLS

(75) Inventors: Shui-on Leung, Madison; Hans Hansen, Mystic Island, both of NJ (US)

(73) Assignee: Immunomedics, Inc., Morris Plains, NJ (US)

(*) Notice: Under 35 U.S.C. 154(b), the term of this patent shall be extended for 0 days.

This patent is subject to a terminal disclaimer.

(21) Appl. No.: 09/127,902

(22) Filed: Aug. 3, 1998

Related U.S. Application Data

(63) Continuation of application No. 08/690,102, filed on Jul. 31, 1996, now Pat. No. 5,789,554, which is a continuation of application No. 08/289,576, filed on Aug. 12, 1994, now abandoned.

(51) Int. Cl.[7] .............. A61K 49/00; A61K 39/395; C12P 21/08; C12N 15/00; C07K 16/30
(52) U.S. Cl. .............. 424/9.1; 424/134.1; 424/135.1; 424/138.1; 424/141.1; 435/69.7; 435/320.1; 530/387.3; 530/388.8; 530/391.7; 536/23.4
(58) Field of Search .............. 530/387.3, 388.8, 530/391.7; 435/320.1, 69.7; 536/23.4; 424/9.1, 134.1, 135.1, 133.1, 138.1, 141.1

(56) References Cited

U.S. PATENT DOCUMENTS 5,057,313 * 10/1991 Shih et al. .................. 424/85.91
5,789,554 * 8/1998 Leung et al. ................ 530/387.3

FOREIGN PATENT DOCUMENTS 0 239 400   9/1987 (EP).

OTHER PUBLICATIONS

Pawlak–Byczkowska, EJ et al. Cancer Research. 49:4568–4577, Aug. 1989.*
Kreitman, RJ et al. Cancer Research. 53:819–825, Feb. 15, 1993.*
Shih, LB et al. Int. J. Cancer. 56:538–545, 1994.*
Goldenberg, DM. J. Clin. Oncology. 9(4):548–564, Apr. 1991.*
Gussow, D and Seeman, G. Meth. in Enzymology. 203:99–121, 1991.*
Morrison, SL et al. Proc. Natl. Acad. Sci. (USA). 81:6851–6855, Nov. 1984.*
Belise et al., "Epitope specificity of the anti–B–cell lymphoma monoclonal antibody, L.L.2" *Proc. of the Am. Assn. for Can. Res.*, vol. 34, p. 481, #2873 (Mar. 1993).
Mills, George Q, M.D., "Diagnostic imaging of non–Hodgkin's B–cell lymphoma with anti–lymphomas antibody labeled with Tc–99m", *Proc. of the Am. Assn. for Can. Res.*, vol. 34, p. 479 (Mar. 1993).
Goldenberg, David M., "Radiolabeled Antibodies", *Scientific. Am. Sci. & Med.*, pp. 64–73, (Mar./Apr. 1994).
Thorpe, Robin, "Monoclonal antibodies: clinical and regulatory issues", *TIBTECH*, vol. 11, pp. 40–42 (Feb. 1993).
Queen et al., *PNAS* 86:10029–10033 (1989).
Baum, et al., *Cancer* 73 (3 Supl): 896–899 (Feb. 1, 1994).
Riechmann, et al., *Nature* 332: 323–327 (1988).

* cited by examiner

Primary Examiner—Christina Y. Chan
Assistant Examiner—F. Pierre VanderVegt
(74) Attorney, Agent, or Firm—Foley & Lardner

(57) ABSTRACT

A chimeric LL2 monoclonal antibody is described in which the complementarity determining regions (CDRs) of the light and heavy chains of the murine LL2 anti-B-lymphoma, anti-leukemia cell monoclonal antibody has been recombinantly joined to the human kappa and $IgG_1$ constant region domains, respectively, which retains the immunospecificity and B-cell lymphoma and leukemia cell internalization capacity of the parental murine LL2 monoclonal antibody, and which has the potential of exhibiting reduced human anti-mouse antibody production activity. A humanized LL2 monoclonal antibody is described in which the CDRs of the light and heavy chains have been recombinantly joined to a framework sequence of human light and heavy chains variable regions, respectively, and subsequently linked to human kappa and $IgG_1$ constant region domains, respectively, which retains the immunospecificity and B-lymphoma and leukemia cell internalization capacities of the parental murine and chimeric LL2 monoclonal antibodies, and which has the potential for exhibiting reduced human anti-mouse antibody production activity. Vectors for producing recombinant chimeric and humanized chimeric monoclonal antibodies are provided. Isolated DNAs encoding the amino acid sequences of the LL2 variable light and heavy chain and CDR framework regions are described. Conjugates of chimeric and humanized chimeric LL2 antibodies with cytotoxic agents or labels find use in therapy and diagnosis of B-cell lymphomas and leukemias.

34 Claims, 17 Drawing Sheets

FIG. 1

```
                         FR1                              L1                        FR2
MURINE      DIOLTQSPSSLAVSAGENVTMSC  KSSQSVLYSANHKNYLA   WYQQKPGQSP
REIHuVK     ----------SA-V--DR----  -----------------   ---------KA-

L2           FR3                                              L3
MURINE      KLLIY  WASTRES  GVPDRFTGSGSGTDFTLTISRVQVEDLAIYYC  HQYLSS
REIHuVK     -----  -------  S----S------F----SL-P----I--T--  ------

FR4
MURINE      WTF  GGGTKLEIKR
REIHuVK     ---  ----------

FR1                                   H1                 FR2
MURINE      QVQLQESGAELSKPGASVKMSCKASGYTFT  SYWLH  WIKQRPGQGLEWIG
EUHuVH1     ---------Q-------------V------  -----  -VR-A---------
EUHuVH2     --------VQ-------------V------  -----  -VR-A---------

H2                            FR3
MURINE      YINPRNDYTEYNQNFKD  KATLTADKSSSTAYMQLSSLTSEDSAVYYCAR
EUHuVH1     ----------------   ---I----E-TN------E----R----T-F-F---
EUHuVH2     ----------------   ---I----E-TN------E----R----T-F-F---

H3           FR4
MURINE      RDITTFY  WGQGTTLTVSS
NEWMHuVH1   -------  -------V---
NEWMHuVH2   -------  -------V---
```

FIG. 4A

```
     GACATTCAGTCTGACCCAGTCTCCATCATCTCTGGCTGTGTCTGCAGGAGAAAACGTCACT
  1  ------+---------+---------+---------+---------+---------+   60
     CTGTAAGTCGACTGGGTCAGAGGTAGTAGAGACCGACACAGACGTCCTCTTTTGCAGTGA

D   I   Q   L   T   Q   S   P   S   S   L   A   V   S   A   G   E   N   V   T

ATGAGCTGTAAGTCCAGTCAAAGTGTTTTATACAGTGCAAATCACAAGAACTACTTGGCC
 61  ------+---------+---------+---------+---------+---------+  120
     TACTCGACATTCAGGTCAGTTTCACAAAATATGTCACGTTTAGTGTTCTTGATGAACCGG

M   S   C  | K   S   S   Q   S   V   L   Y   S   A   N   H   K   N   Y   L   A |
                                           CDR1

TGGTACCAGCAGAAACCAGGGCAGTCTCCTAAACTGCTGATCTACTGGGCATCCACTAGG
121  ------+---------+---------+---------+---------+---------+  180
     ACCATGGTCGTCTTTGGTCCCGTCAGAGGATTTGACGACTAGATGACCCGTAGGTGATCC

W   Y   Q   Q   K   P   G   Q   S   P   K   L   L   I   Y  | W   A   S   T   R |
                                                                         CDR2

GAATCTGGTGTCCCTGATCGCTTCACAGGCGGATCTGGGACAGATTTTACTCTTACC
181  ------+---------+---------+---------+---------+---------+  240
     CTTAGACCACAGGGACTAGCGAAGTGTCCGTCCTAGACCCTGTCTAAAATGAGAATGG

E   S | G   V   P   D   R   F   T   G   S   G   S   G   T   D   F   T   L   T

ATCAGCAGAGTACAAGTTGAAGACCTGGCAATTTATTATTGTCACCAATACCTCTCCTCG
241  ------+---------+---------+---------+---------+---------+  300
     TAGTCGTCTCATGTTCAACTTCTGGACCGTTAAATAATAACAGTGGTTATGGAGAGGAGC

I   S   R   V   Q   V   E   D   L   A   I   Y   Y   C | H   Q   Y   L   S   S |
                                                                     CDR3

TGGACGTTCGGTGGAGGGACCAAGCTGGAGATCAAACGT
301  ------+---------+---------+---------+   339
     ACCTGCAAGCCACCTCCCTGGTTCGACCTCTAGTTTGCA

| W   T   F | G   G   G   T   K   L   E   I   K   R
```

FIG. 4B

```
    CAGGTCCAGCTGCAGGAGTCAGGGGCTGAACTGTCAAAACCTGGGGCCTCAGTGAAGATG
  1 ------+---------+---------+---------+---------+---------+ 60
    GTCCAGGTCGACGTCCTCAGTCCCCGACTTGACAGTTTTGGACCCCGGAGTCACTTCTAC

Q  V  Q  L  Q  E  S  G  A  E  L  S  K  P  G  A  S  V  K  M -

TCCTGCAAGGCTTCTGGCTACACCTTTACTAGCTACTGGCTGCACTGGATAAAACAGAGG
 61 ------+---------+---------+---------+---------+---------+ 120
    AGGACGTTCCGAAGACCGATGTGGAAATGATCGAAATGATCGACCGACGTGACCTATTTTGTCTCC

S  C  K  A  S  G  Y  T  F  T │ S  Y  W  L  H │ W  I  K  Q  R -
                                   └─── CDR1 ────┘

CCTGGACAGGGTCTGGAATGGATTGGATACATTAATCCTAGGAATGATTATACTGAGTAC
121 ------+---------+---------+---------+---------+---------+ 180
    GGACCTGTCCCAGACCTTACCTAACCTATGTAATTAGGATCCTTACTAATATGACTCATG

P  G  Q  G  L  E  W  I  G │ Y  I  N  P  R  N  D  Y  T  E  Y -
                                └──────── CDR2 ──────────┘

AATCAGAACTTCAAGGACAAGGCCACACTGACTGCAGACAAATCCTCCAGCACAGCCTAC
181 ------+---------+---------+---------+---------+---------+ 240
    TTAGTCTTGAAGTTCCTGTTCCGGTGTGACTGACGTCTGTTTAGGAGGTCGTGTCGGATG

│ N  Q  N  F  K  D │ K  A  T  L  T  A  D  K  S  S  S  T  A  Y -
    └──────────────────┘

ATGCAACTGAGCAGCCTGACATCTGAGGACTCTGCAGTCTATTACTGTGCAAGAAGGGAT
241 ------+---------+---------+---------+---------+---------+ 300
    TACGTTGACTCGTCGGACTGTAGACTCCTGAGACGTCAGATAATGACACGTTCTTCCCTA

M  Q  L  S  S  L  T  S  E  D  S  A  V  Y  Y  C  A  R │ R  D │-
                                                          └──────┘

ATTACTACGTTCTACTGGGGCCAAGGCACCACTCTCACAGTCTCCTCG
301 ------+---------+---------+---------+-------     348
    TAATGATGCAAGATGACCCCGGTTCCGTGGTGAGAGTGTCAGAGGAGC

│ I  T  T  F  Y │ W  G  Q  G  T  T  L  T  V  S  S -
    └─── CDR3 ─────┘
```

FIG. 5A

```
     GACATTCAGCTGACCCAGTCTCCATCATCTCTGAGCGCCATCTGTTGGAGATAGGGTCACT
  1  ------+---------+---------+---------+---------+---------+   60
     CTGTAAGTCGACTGGGTCAGAGGTAGTAGAGACTCGCGGTAGACAACCTCTATCCCAGTGA
      D   I   Q   L   T   Q   S   P   S   S   L   S   A   S   V   G   D   R   V   T  -

ATGAGCTGTAAGTCCAGTCAGTCAAAGTGTTTTATACAGTGCAAATCACAAGAACTACTTGGCC
 61  ------+---------+---------+---------+---------+---------+  120
     TACTCGACATTCAGGTCAGTCAGTTTCACAAAATATGTCACGTTTAGTGTTCTTGATGAACCGG
      M   S   C   K   S   S   Q   S   V   L   Y   S   A   N   H   K   N   Y   L   A  -
                      |CDR1                                           |

TGGTACCAGCAGAAACCAGGGAAAGCACCTAAACTGCTGATCTACTGGGCATCCACTAGG
121  ------+---------+---------+---------+---------+---------+  180
     ACCATGGTCGTCTTTGGTCCCTTTCGTGGATTTGACGACTAGATGACCCGTAGGTGATCC
      W   Y   Q   Q   K   P   G   K   A   P   K   L   L   I   Y  |W   A   S   T   R| -
                                                                  CDR2

GAATCTGGTGTCCCTTCGGATTCTCTGGCAGCGGATCTGGGACAGATTTTACTTTCACC
181  ------+---------+---------+---------+---------+---------+  240
     CTTAGACCACAGGGAAGCCTAAGACGCCGTCGCCTAGAGACCCGTCGCCTAGAGTGG
     |E   S| G   V   P   S   R   F   S   G   S   G   S   G   T   D   F   T   F   T  -

ATCAGCTCTCTTCAACCAGAAGACATTGCAACAGTTGTATAATAACAGTGGTTATGGAGAGAGC
241  ------+---------+---------+---------+---------+---------+  300
     TAGTCGAGAGAAGTTGGTCTTCTGTAACGTTGTCAACATATTATTGTCACCAATACCCTCTCG
      I   S   S   L   Q   P   E   D   I   A   T   Y   Y   C  |H   Q   Y   L   S   S| -
                                                              CDR3

TGGACGTTCGGTGGAGGGACCAAGCTGGAGATCAAACGT
301  ------+---------+---------                               339
     ACCTGCAAGCCACCTCCCCTGGTTCGACCTCTAGTTTGCA
     |W   T   F| G   G   G   T   K   L   E   I   K   R
```

FIG. 5B

```
    CAGGTCCAGCTGGTCCAATCAGGGGCTGAAGTCAAGAAACCTGGGTCATCAGTGAAGGTC
  1 ----+----+----+----+----+----+----+----+----+----+----+----+  60
    GTCCAGGTCGACCAGGTTAGTCCCCGACTTCAGTCTTTGGACCCAGTAGTCACTTCCAG

Q  V  Q  L  V  Q  S  G  A  E  V  K  K  P  G  S  S  V  K  V

TCCTGCAAGGCTTCTGGCTACACCTTTACTAGCTACTGGCTGCACTGGGTCAGGCAGGCA
 61 ----+----+----+----+----+----+----+----+----+----+----+----+ 120
    AGGACGTTCCGAAGACCGATGTGGAAATGATCGATGACCGACGTGACCCAGTCCGTCCGT

S  C  K  A  S  G  Y  T  F  T │ S  Y  W  L  H │ W  V  R  Q  A
                                   └── CDR1 ──────┘

CCTGGACAGGGTCTGGAATGGATTGGATACATTAATCCTAGGAATGATTATACTGAGTAC
121 ----+----+----+----+----+----+----+----+----+----+----+----+ 180
    GGACCTGTCCCAGACCTTACCTAACCTATGTAATTAGGATCCTTACTAATATGACTCATG

P  G  Q  G  L  E  W  I  G │ Y  I  N  P  R  N  D  Y  T  E  Y
                                └────────── CDR2 ────────────────

AATCAGAACTTCAAGGACAGCCTGAGGTCTGAGGACACGGCCATTTATTTTTGTGCAAGAAGGGAT
181 ----+----+----+----+----+----+----+----+----+----+----+----+ 240
    TTAGTCTTGAAGTTCCTGTCGGACTCCAGACTCCTGTGCCGGTAAATAAAAACACGTTCTTCCCTA

│ N  Q  N  F  K  D │ K  A  T  I  T  A  D  E  S  T  N  T  A  Y │
   └──── CDR2 ────────┘

ATGGAGCTGAGCAGCCTGAGGTCTGAGGACACGGCCATTTATTTTTGTGCAAGAAGGGAT
241 ----+----+----+----+----+----+----+----+----+----+----+----+ 300
    TACCTCGACTCGTCGGACTCCAGACTCCTGTGCCGGTAAATAAAAACACGTTCTTCCCTA

M  E  L  S  S  L  R  S  E  D  T  A  F  Y  F  C  A  R │ R  D │

ATTACTACGTTCTACTGGGGCCAAGGCACCACGGTCACCGTCTCCTCG
301 ----+----+----+----+----+----+----+----+-------- 348
    TAATGATGCAAGATGACCCCGGTTCCGTGGTGCCAGTGGCAGAGGAGC

│ I  T  T  F  Y │ W  G  Q  G  T  T  V  T  V  S  S
   └── CDR3 ───────┘
```

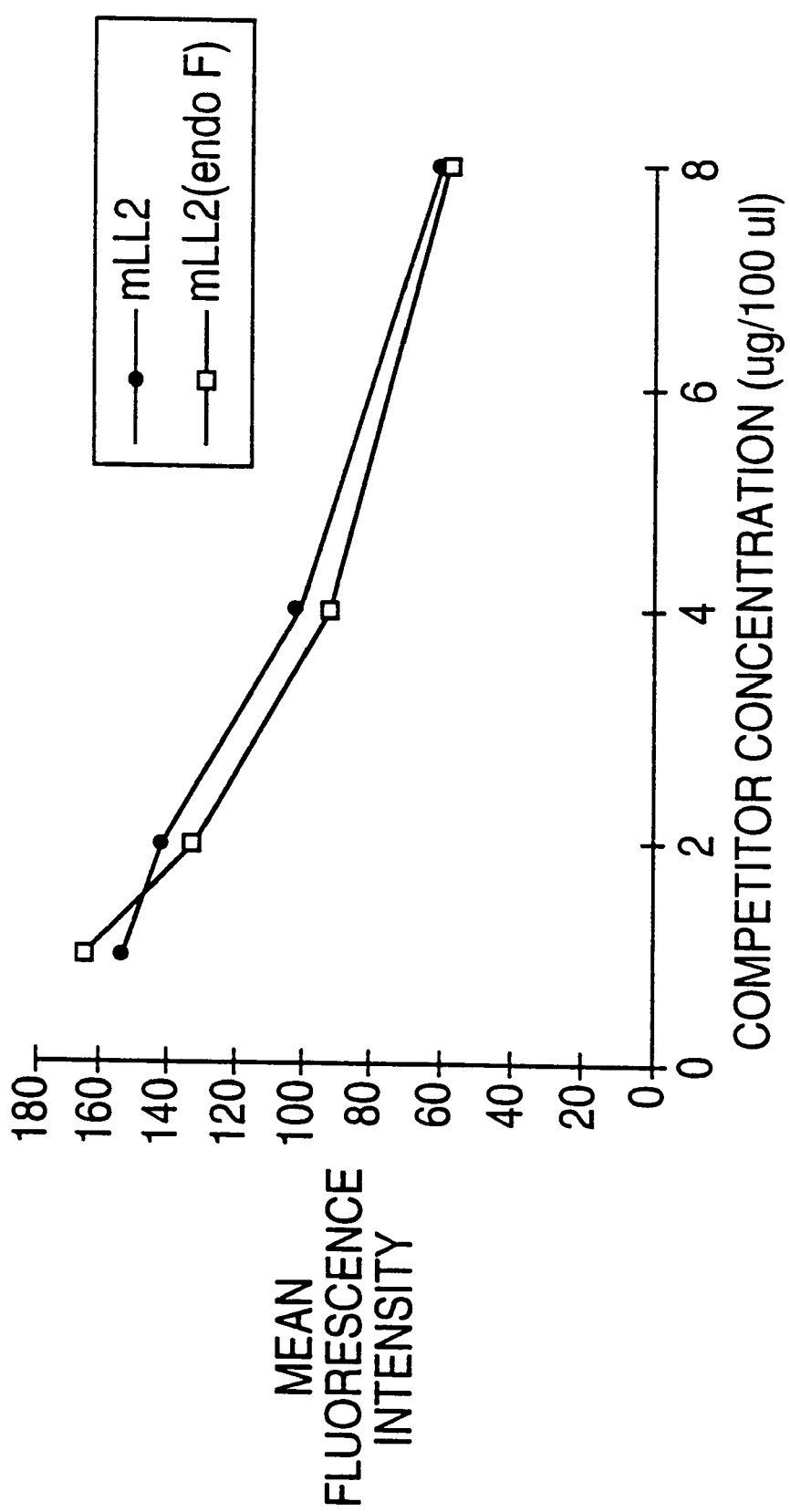

IMMUNOCONJUGATES AND HUMANIZED ANTIBODIES SPECIFIC FOR B-CELL LYMPHOMA AND LEUKEMIA CELLS

This application is a continuation of application Ser. No. 08/690,102, filed Jul. 31, 1996, now U.S. Pat. No. 5,789,554, which is in turn a continuation of Ser. No. 08/289,576, filed Aug. 12, 1994 now abandoned.

BACKGROUND OF THE INVENTION

The invention relates generally to immunoconjugates for diagnostic and therapeutic uses in cancer. In particular, the invention relates to recombinantly produced chimeric and humanized monoclonal antibodies directed against B-cell lymphoma and leukemia cells, which antibodies can be covalently conjugated to a diagnostic or therapeutic reagent without loss of antibody binding and internalization function and with reduced production of human anti-mouse antibodies.

Non-Hodgkins lymphoma (NHL) and chronic lymphocytic leukemia are B-cell malignancies that remain important contributors to cancer mortality. The response of these malignancies to various forms of treatment is mixed. They respond reasonably well to chemotherapy, and, in cases where adequate clinical staging of NHL is possible, as for patients with localized disease, satisfactory treatment may be provided using field radiation therapy (Hall et al., *Radiology for the Radiologist*, Lippincott, Philadelphia, 1989, pp 365–376). However, the toxic side effects associated with chemotherapy and the toxicity to the hematopoietic system from local, as well as whole body, radiotherapy, limits the use of these therapeutic methods. About one-half of the patients die from the disease (Posner et al., *Blood*, 61: 705 (1983)).

The use of targeting monoclonal antibodies conjugated to radionuclides or other cytotoxic agents offers the possibility of delivering such agents directly to the tumor site, thereby limiting the exposure of normal tissues to toxic agents (Goldenberg, *Semin. Nucl. Med.*, 19: 332 (1989)). In recent years, the potential of antibody-based therapy and its accuracy in the localization of tumor-associated antigens have been demonstrated both in the laboratory and clinical studies (see., e.g., Thorpe, *TIBTECH*, 11: 42 (1993); Goldenberg, *Scientific American, Science & Medicine*, 1: 64 (1994); Baldwin et al., U.S. Pat. No. 4,925,922 and 4,916,213; Young, U.S. Pat. No. 4,918,163; U.S. Pat. No. 5,204,095; Irie et al., U.S. Pat. No. 5,196,337; Hellstrom et al., U.S. Pat. Nos. 5,134,075 and 5,171,665). In general, the use of radio-labeled antibodies or antibody fragments against tumor-associated markers for localization of tumors has been more successful than for therapy, in part because antibody uptake by the tumor is generally low, ranging from only 0.01% to 0.001% of the total dose injected (Vaughan et al., *Brit. J. Radiol.*, 60: 567 (1987)). Increasing the concentration of the radiolabel to increase the dosage to the tumor is counterproductive generally as this also increases exposure of healthy tissue to radioactivity.

LL-2 (EPB2) is a highly specific anti-B-cell lymphoma and anti-lymphocytic leukemia cell murine monoclonal antibody (mAb) that is rapidly internalized by such cells and that can overcome some of the aforementioned difficulties (Shih et al., *Int. J. Cancer*, 56: 538 (1994)). LL2, which is of the IgG2a antibody type, was developed using the Raji B-lymphoma cell line as the source of antigen (Pawlak-Byczkowska et al., *Cancer Res.*, 49: 4568 (1989)). Murine LL2 (mLL2) is known to react with an epitope of CD22 (Belisle et al., *Proc Amer. Assn. Clin. Res.*, 34: A2873 (1993)). CD22 molecules are expressed in the cytoplasm of progenitor and early pre-B cells, and appear in the cell surface of mature B-cells.

By immunostaining of tissue sections, mLL2 was shown to react with 50 of 51 B-cell lymphomas tested. mLL2 is a highly sensitive means of detecting B-cell lymphoma cell in vivo, as determined by a radioimmunodetection method (Murthy et al., *Eur. J. Nucl. Med.*, 19: 394 (1992)). The Fab' fragment of mLL2 labeled with $^{99m}$Tc localized to 63 of 65 known lesions in Phase II trial patients with B-cell lymphoma (Mills et al., *Proc. Amer. Assn. Cancer Res.*, 14: A2857 (1993)). In addition, $^{131}$I-labeled mLL2 was therapeutically effective in B-cell lymphoma patients (Goldenberg et al., *J. Clin. Oncol.*, 9: 548 (1991)). mLL2 Fab' conjugated to the exotoxin PE38KDEL induced complete remissions of measurable human lymphoma xenografts (CA-46) growing in nude mice (Kreitman et al., *Cancer Res.*, 53: 819 (1993)).

The clinical use of mLL2, just as with most other promising murine antibodies, has been limited by the development in humans of a HAMA response. While a HAMA response is not invariably observed following injection of mLL2, in a significant number of cases patients developed HAMA following a single treatment with mLL2. This can limit the diagnostic and therapeutic usefulness of such antibody conjugates, not only because of the potential anaphylactic problem, but also as a major portion of the circulating conjugate may be complexed to and sequestered by the circulating anti-mouse antibodies. This is exemplified by one study in which about 30% of the patients developed low level HAMA response following a single injection of about 6 mg of mLL2 $^{131}$I-IgG and nearly all developed a strong HAMA response with additional injections. On the other hand, with mLL2 Fab' labeled with $^{99m}$Tc, no HAMA response was observed. Such HAMA responses in general pose a potential obstacle to realizing the full diagnostic and therapeutic potential of the mLL2 antibody.

Although, as noted above, the use of fragments of mLL2, such as F(ab')$_2$ and Fab', partially alleviate/circumvent these problems of immunogenicity, there are circumstances in which whole IgG is more desirable, such as when induction of cellular immunity is intended for therapy, or where an antibody with enhanced survival time is required.

In order to maximize the value of the mLL2 IgG antibody as a therapeutic or diagnostic modality and increase its utility in multiple and continuous administration modalities, it is an object of this invention to produce a mouse/human chimeric mAb (cLL2) and a humanized mAb (hLL2) related to mLL2 that retain the antigen-binding specificity of mLL2, but that elicit reduced HAMA in a subject receiving same.

It is another object of this invention to provide DNA sequences encoding the amino acid sequences of the variable regions of the light and heavy chains of the cLL2 and hLL2 mabs, including the complementarity determining regions (CDR).

It is also an object of this invention provide conjugates of the hLL2 and cLL2 mAbs containing therapeutic or diagnostic modalities.

It is a further object of this invention to provide methods of therapy and diagnosis that utilize the humanized and chimeric mabs of the invention.

These objects have been achieved by the invention described below in the specification and appended claims.

SUMMARY OF THE INVENTION

In one aspect of the invention, there is provided a cLL2 mAb related to mLL2 mAb, in which the murine light (VK)

and heavy (VH) chain variable regions are joined to the human constant light (kappa) and heavy (IgG₁) chains. This chimeric mAb retains the B-lymphoma and leukemia cell targeting and internalization properties of the parental mLL2.

In another aspect of the invention, there is provided a hLL2 mAb related to mLL2 mAb, in which the complementarity-determining regions (CDRs) of the light and heavy chains of the mLL2 mAb are joined to the framework (FR) sequence of human VK and VH regions, respectively, and subsequently to the human kappa and IgG₁ constant region domains, respectively. This humanized antibody retains the B-lymphoma and leukemia cell targeting and internalization characteristics of the parental mLL2 mAb, and can exhibit a lowered HAMA reaction.

In still another aspect, there is provided isolated polynucleotides comprising DNA sequences encoding the amino acid sequences of the variable light and heavy chains, respectively, of the hLL2 and cLL2 mAbs.

In an additional aspect, there is provided the amino acid sequences of the CDRs of the VK and VH chains.

In yet another aspect, there are provided conjugates in which the hLL2 or cLL2 mAb is covalently bonded to a diagnostic or therapeutic reagent.

In still another aspect, there are provided methods whereby the aforementioned mAb conjugates can be used to diagnose or treat B-cell lymphomas and lymphocytic leukemias.

These and other aspects and embodiments of the invention will become apparent by reference to the following specification and appended claims.

DESCRIPTION OF THE FIGURES

FIG. 1 shows a comparison of the amino acid sequences between murine LL2 and humanized LL2REIHuVK (FIG. 1A, SEQ ID NOS. 2 and 6) and between murine LL2 and humanized EUHuVH1 and EUHuVH2, and NEWMHuVH1 and NEWMHuVH2 (FIG. 1B, SEQ ID NOS. 4, 9 and 8). Asterisks indicate murine LL2 sequences that are different from that of the human FR at corresponding positions. CDRs are boxed. FR residues showing CDR contacts by computer modeling are underlined.

FIG. 3A shows the light chain staging (VKpBR) and mammalian expression (pKH) vectors, and while

FIG. 4 shows the double-stranded DNA and amino acid sequences of the LL2 VK domain (FIG. 4A) and the LL2 VH domain (FIG. 4B SEQ. ID NOS. 3 and 4). Amino acid sequences encoded by the corresponding DNA sequences are given as one letter codes. CDR amino acid sequences are boxed. The Asn-glycosylation site located in FR1 of LL2VK (FIG. 4A SEQ. ID NO. 2) is shown as the underlined NVT sequence.

FIG. 5A shows the double stranded DNA and corresponding amino acid residues of the hLL2 VK domain (SEQ. ID NOS. 5 and 6). CDR amino acid sequences are boxed. The corresponding data for the VH domain is shown in FIG. 5B (SEQ. ID NOS. 7 and 8).

FIG. 11A shows the results of a comparative Raji cell competitive antibody binding assay in which mixed humanized/chimeric LL2s were compared to cLL2, while

FIG. 14 shows the effect of deglycosylation of mLL2 on its binding affinity to Raji cells.

Figure 2A:
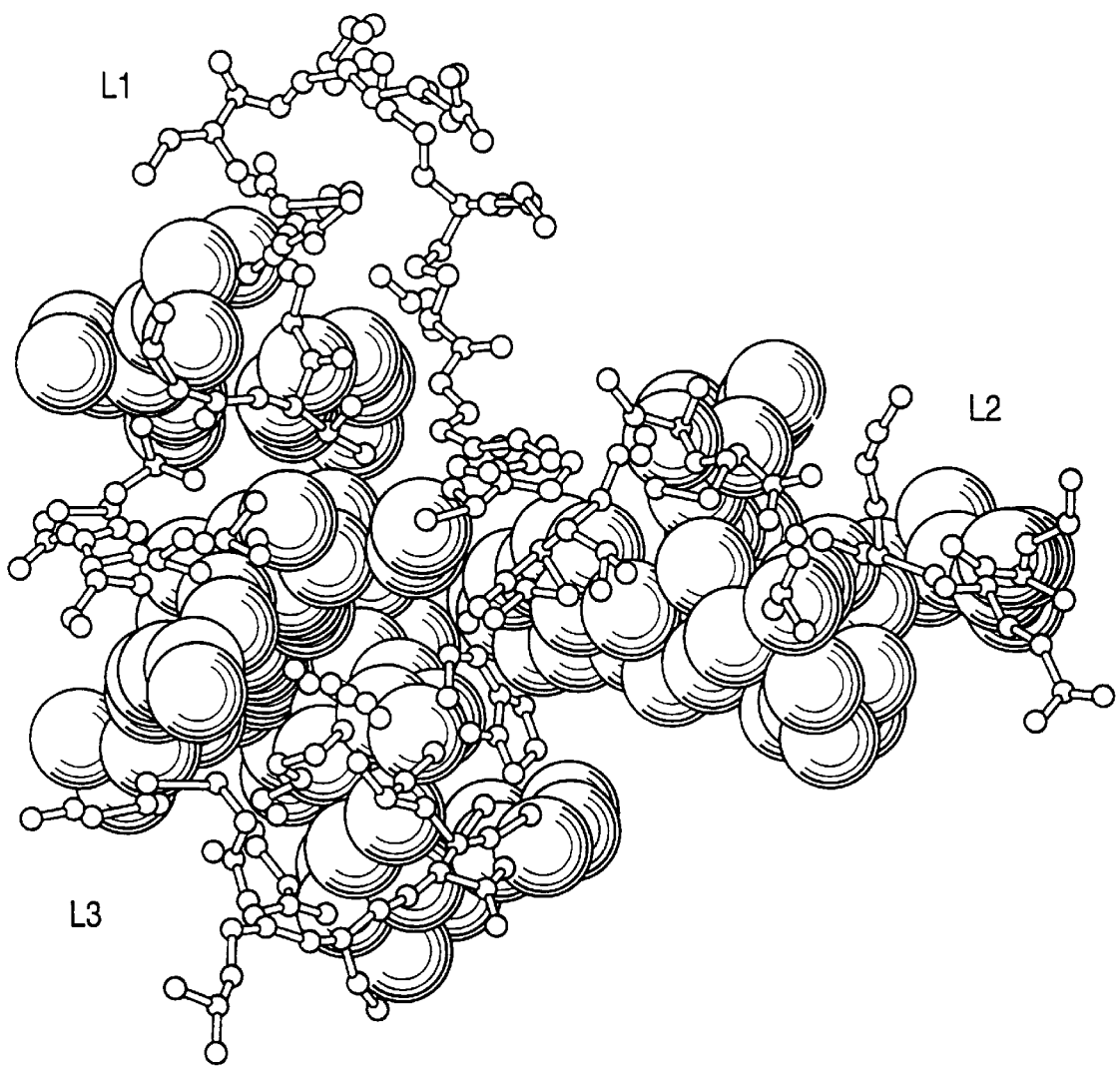
FIG. 2 shows vicinal relationships of the LL2 CDRs to their framework regions (FRs). Separate energy-minimized models for the VL and VK domains of mLL2 were constructed, and all FR residues within a radius of 4.5 Å or any CDR atom were identified as potential CDR-FR contacts. CDRs of the light (L1, L2, and L3, FIG. 2A) and heavy (H1, H2, and H3, FIG. 2B)) chains are shown as "ball and stick" representations superimposed on their respective, space-filling FRs.

DETAILED DESCRIPTION OF THE INVENTION cDNAs encoding the VL and VH regions of the mLL2 mAb have been isolated and separately recombinantly subcloned into mammalian expression vectors containing the genes encoding kappa and IgG₁ constant regions, respectively, of human antibodies. Cotransfection of mammalian cells with these two recombinant DNAs expressed a cLL2 mAb that, like the parent mLL2 mAb, bound avidly to, and was rapidly internalized by, B-lymphoma cells.

The CDRs of the VK and VH DNAs have been similarly recombinantly linked to the framework (FR) sequences of the human VK and VH regions, respectively, which are subsequently linked, respectively, to the human kappa and IgG₁ constant regions, so as to express in mammalian cells as described above hLL2.

In this specification, the expressions "cLL2" or "cLL2 mAb" are intended to refer to the chimeric monoclonal antibody constructed by joining or subcloning the murine VK and VH regions to the human constant light and heavy chains, respectively. The expressions "hLL2" or "hLL2 mAb" are intended to refer to the humanization of the chimeric monoclonal antibody by replacing the murine FR sequences in cLL2 with that of human framework regions.

Covalent conjugates between cLL2 and hLL2 mAbs and a diagnostic or chemotherapeutic reagent, formulated in pharmaceutically acceptable vehicles (see, e.g., *Remington's Pharmaceutical Sciences,* 18th ed., Mack Publishing Co., Easton, Pa., 1990) can be prepared that have the advantages, compared to prior art antibody conjugates, of B-cell lymphoma-specific and leukemia cell-specific targeting, rapid internalization into target cells, rapid liberation of the diagnostic or chemotherapeutic reagent intracellularly (thereby increasing effectiveness of the reagent), and a potential reduction of the HAMA response in the human patient.

As the VK-appended carbohydrate moiety of the cLL2 mAb is shown herein not to be involved in binding to B-lymphoma cells, it is preferred to use conjugates in which the reagent is bound to the antibody through such carbohydrate moieties, such as through oxidized carbohydrate derivatives. Methods for the production of such conjugates and their use in diagnostics and therapeutics are provided, for example. in Shih et al., U.S. Pat. No. 5,057,313, Shih et al., *Int. J. Cancer* 41: 832 (1988), and copending, commonly owned Hansen et al., U.S. Ser. No. 08/162,912, the contents of which are incorporated herein by reference. Direct linkage of the reagent to oxidized carbohydrate without the use of a polymeric carrier is described in McKearn et al., U.S. Pat. No. 5,156,840, which is also incorporated by reference.

A wide variety of diagnostic and therapeutic reagents can be advantageously conjugated to the antibodies of the invention. These include: chemotherapeutic drugs such as doxorubicin, methotrexate, taxol, and the like; chelators, such as DTPA, to which detectable labels such as fluorescent molecules or cytotoxic agents such as heavy metals or radionuclides can be complexed; and toxins such as Pseudomonas exotoxin, and the like. Several embodiments of these conjugates are described in the examples below.

Cell lines and culture media used in the present invention include LL2 (EPB-2) hybridoma cells (Pawlak-Byczkowska et al. 1989 above), Sp2/0-Ag14 myeloma cells (ATCC, Rockville, Md.) and Raji cells. These cells are preferably cultured in Dulbecco's modified Eagle's Medium (DMEM) supplemented with 10% FCS (Gibco/BRL, Gaithersburg, Mass.), 2 mM L-glutamine and 75 μg/ml gentamicin, (complete DMEM). Transfectomas are grown in Hybridoma Serum Free Medium, HSFM, (Gibco/BRL, Gaithersburg, Mass.) containing 10% of FCS and 75 μg/ml gentamicin (complete HSFM) or, where indicated, in HSFM containing only antibiotics. Selection of the transfectomas may be carried out in complete HSFM containing 500 μg/ml of hygromycin (Calbiochem, San Diego, Calif.). All cell lines are preferably maintained at 37° C. in 5% $CO_2$.

An important aspect of this invention is that antibody variable domains can be modeled by computer modeling (see, for example, Dion, in Goldenberg et al. eds., *Cancer Therapy With Radiolabeled Antibodies*, CRC Press, Boca Raton, Fla., 1994), which is incorporated by reference. In general, the 3-D structure for both the mLL22 and hLL2 mabs are best modeled by homology. The high frequency of residue identities (75.0 to 92.3%) between the deduced primary sequences of mLL2 light chain FR regions and human REI (VK) facilitates this approach because of the availability of crystallographic data from the Protein Data Bank (PDR Code 1REI, Bernstein et al., *J. Mol. Biol.* 112: 535 (1977)), which is incorporated by reference. Similarly, antibody EU (VH) sequences can be selected as the computer counterparts for FR1 to FR3 of the mLL2 heavy chain; FR4 was based on NEWM. As X-ray coordinate data is currently lacking for the EU sequence, NEWM structural data (PDR Code 3FAB) for FRs 1 to 4 can be used, and amino acid side groups can be replaced to correspond to mLL2 or EU (hLL2) as needed. The CDR of the light chain can be modeled from the corresponding sequence of 1MCP (L1 and L2) and 1REI (L3). For heavy chain CDRs, H1 and H2 can be based on 2HFL and 1MCP, respectively, while H3 can be modeled de novo. Wherever possible, side group replacements should be performed so as to maintain the torsion angle between Cα and Cβ. Energy minimization may be accomplished by the AMBER forcefield (Weiner et al, *J. Amer. Chem. Soc.* 106: 765 (1984) using the convergent method. Potentially critical FR-CDR interactions can be determined by initially modeling the light and heavy variable chains of mLL2. All FR residues within a 4.5 Å radius of all atoms within each CDR can thereby be identified and retained in the final design model of hLL2.

Once the sequences for the hLL2 VK and VH domains are designed, CDR engrafting can be accomplished by gene synthesis using long synthetic DNA oligonucleotides as templates and short oligonucleotides as primers in a PCR reaction. In most cases, the DNA encoding the VK or VH domain will be approximately 350 bp long. By taking advantage of codon degeneracy, a unique restriction site may easily be introduced, without changing the encoded amino acids, at regions close to the middle of the V gene DNA sequence. For example, at DNA nucleotide positions 157–162 (amino acid positions 53 and 54) for the hLL2 VH domain, a unique AvrII site can be introduced while maintaining the originally designed amino acid sequence (FIG. 4B). Two long non-overlapping single-stranded DNA oligonucleotides (~150 bp) upstream and downstream of the AvrII site (see, for example, oligo A and oligo B, Example 3 below) can be generated by automated DNA oligonucleotide synthesizer (Cyclone Plus DNA Synthesizer, Milligen-Biosearch). As the yields of full length DNA oligonucleotides such as oligos A and B may be expected to be low, they can be amplified by two pairs of flanking oligonucleotides (oligo Seq. ID Nos. 10 and 11 for oligo A; oligo Seq. ID Nos. 12 and 13 for oligo B, Example 3) in a PCR reaction. The primers can be designed with the necessary restriction sites to facilitate subsequent subcloning. Primers for oligo A and for oligo B should contain overlapping sequence at the AvrII site so that the resultant PCR product for oligo A and B, respectively, can be joined in-frame at the AvrII site to form a full length DNA sequence (ca 350 bp) encoding the hLL2 VH domain. The ligation of the PCR products for oligo A (restriction-digested with PstI and AvrII) and B (restriction-digested with AvrII and EstEII) at the AvrII site and their subcloning into the PstII/BstEII sites of the staging vector, VHpBS, can be completed in a single three-fragment-ligation step (See, for example, Example 3). The subcloning of the correct sequence into VHpBS can be first analyzed by restriction digestion analysis and subsequently confirmed by sequencing reaction according to Sanger et al., *Proc. Natl. Acad. Sci. USA* 74: 5463 (1977).

The HindIII/BamHI fragment containing the Ig promoter, leader sequence and the hLL2 VH sequence can be excised from the staging vector and subcloned to the corresponding sites in a pSVgpt-based vector, pG1g, which contains the genomic sequence of the human IgG constant region, an Ig enhancer and a gpt selection marker, forming the final expression vector, hLL2pG1g. Similar strategies can be employed for the construction of the hLL2 VK sequence. The restriction site chosen for the ligation of the PCR products for the long oligoncloetides (oligos C and D, see examples below) can be NruI in this case.

The DNA sequence containing the Ig promoter, leader sequence and the hLL2 VK sequence can be excised from the staging vector VKPBR by treatment with BamHI/HindIII, and can be subcloned into the corresponding sites of a pSVhyg-based vector, pKh, which contains the genomic sequence of human kappa chain constant regions, a hygromycin selection marker, an Ig and a kappa enhancer, forming the final expression vector, hLL2pKh.

As humanization sometimes results in a reduction or even loss of antibody affinity, additional modification might be required in order to restore the original affinity (See, for example, Tempest et al., *Bio/Technology* 9: 266 (1991); Verhoeyen et al., *Science* 239: 1534 (1988)), which are incorporated by reference. Knowing that cLL2 exhibits a binding affinity comparable to that of its murine counterpart (see Example 5 below), defective designs, if any, in the original version of hLL2 can be identified by mixing and matching the light and heavy chains of cLL2 to those of the humanized version. SDS-PAGE analysis of the different mix-and-match humanized chimeric LL2 under non-reducing (the disulfide L-H chain connections remain intact) and reducing conditions (the chains separate, permitting analyses of the relationships of the different types of light and heavy chains on the properties of the molecule). For example, migration as multiple bands or as a higher apparent molecular size can be due to the presence of a glycan group at the N-linked glycosylation site found at the FR1 region of the murine VK domain of LL2. For another example, a discrete band migrating at about 25 kDa is the expected molecular size for a non-glycosylated light chain.

In general, to prepare cLL2 mAb, VH and VK chains of mLL2 can be obtained by PCR cloning using DNA products and primers. Orlandi et al., infra, and Leung et al., infra. The VK PCR primers may be subcloned into a pBR327 based staging vector (VKpBR) as described above. The VH PCR products may be subcloned into a similar pBluescript-based staging vector (VHpBS) as described above. The fragments containing the VK and VH sequences, along with the promoter and signal peptide sequences, can be excised from the staging vectors using HindIII and BamHI restriction endonucleases. The VK fragments (about 600 bp) can be subcloned into a mammalian expression vector (for example, pKh) conventionally. pKh is a pSVhyg-based expression vector containing the genomic sequence of the human kappa constant region, an Ig enhancer, a kappa enhancer and the hygromucin-resistant gene. Similarly, the about 800 bp VH fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be transfected into mammalian expression cells, such as Sp2/0-Ag14 cells, by electroporation and selected for hygromycin resistance. Colonies surviving selection are expanded, and supernatant fluids monitored for production of cLL2 mAb by an ELISA method. A transfection efficiency of about $1-10 \times 10^6$ cells is desirable. An antibody expression level of between 0.10 and 2.5 $\mu$g/ml can be expected with this system.

RNA isolation, cDNA synthesis, and amplification can be carried out as follows. Total cell RNA can be prepared from a LL2 hybridoma cell line, using a total of about $10^7$ cells, according to Sambrook et al., (*Molecular Cloning: A Laboratory Manual*, Second ed., Cold Spring Harbor Press, 1989), which is incorporated by reference. First strand cDNA can be reverse transcribed from total RNA conventionally, such as by using the SuperScript preamplification system (Gibco/BRL., Gaithersburg, Md.). Briefly, in a reaction volume of 20 $\mu$l, 50 ng of random primers can be annealed to 5 $\mu$g of RNAs in the presence of 2 $\mu$l of 10× synthesis buffer [200 mM Tris-HCl (pH 8.4), 500 mM KCl, 25 mM MgCl$_2$, 1 mg/ml BSA], 1 $\mu$l of 10 mM dNTP mix, 2 $\mu$l of 0.1 M DTT, and 200 units of SuperScript reverse transcriptase. The elongation step is initially allowed to proceed at room temperature for 10 min followed by incubation at 42° C. for 50 min. The reaction can be terminated by heating the reaction mixture at 90° C. for 5 min.

The VK and VH sequences for cLL2 or hLL2 can amplified by PCR as described by Orlandi et al., (*Proc. Natl. Acad. Sci.*, U.S.A., 86: 3833 (1989)) which is incorporated by reference. VK sequences may be amplified using the primers CK3BH and VK5-3 (Leung et al., *BioTechniques*, 15: 286 (1993), which is incorporated by reference), while VH sequences can be amplified using the primer CH1B which anneals to the CH1 region of murine IgG, and VHIBACK (Orlandi et al., 1989 above). The PCR reaction mixtures containing 10 $\mu$l of the first strand cDNA product, 9 $\mu$l of 10× PCR buffer [500 mM KCl, 100 mM Tris-HCl (pH 8.3), 15 mM MgCl2, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). See Example 3 for a method for the synthesis of an oligo A (149-mer) and an oligo B (140-mer) on an automated Cyclone Plus DNA synthesizer (Milligan-2iosearch) for use in constructing humanized V genes.

PCR products for VK can be subcloned into a staging vector, such as a pBR327-based staging vector VKpBR that contains an Ig promoter, a signal peptide sequence and convenient restriction sites to facilitate in-frame ligation of the VK PCR products. PCR products for VH can be subcloned into a similar staging vector, such as the pbluescript-based VHpBS. Individual clones containing the respective PCR products may be sequenced by, for example, the method of Sanger et al., *Proc. Natl. Acad. Sci.*, U.S.A., 74: 5463 (1977) which is incorporated by reference.

The DNA sequences described herein are to be taken as including all alleles, mutants and variants thereof, whether occurring naturally or induced.

The two plasmids can be co-transfected into an appropriate cell, e.g., myeloma Sp2/0-Ag14, colonies selected for hygromycin resistance, and supernatant fluids monitored for production of cLL2 or hLL2 antibodies by, for example, an ELISA assay, as described below.

Transfection, and assay for antibody secreting clones by ELISA, can be carried out as follows. About 10 $\mu$g of hLL2pKh (light chain expression vector) and 20 $\mu$g of hLL2pG1g (heavy chain expression vector) can be used for the transfection of $5 \times 10^6$ SP2/0 myeloma cells by electroporation (BioRad, Richmond, Calif.) according to Co et al., *J. Immunol.*, 148: 1149 (1992) which is incorporated by reference. Following transfection, cells may be grown in 96-well microtiter plates in complete HSFM medium (GIBCO, Gaithersburg, Md.) at 37° C., 5% CO$_2$. The selection process can be initiated after two days by the addition of hygromycin selection medium (Calbiochem, San Diego, Calif.) at a final concentration of 500 $\mu$g/ml of hygromycin. Colonies typically emerge 2–3 weeks post-electroporation. The cultures can then be expanded for further analysis.

Transfectoma clones that are positive for the secretion of chimeric or humanized heavy chain can be identified by ELISA assay. Briefly, supernatant samples (100 $\mu$l) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 μl of antibody stock diluted×10⁴, supplemented with the unconjugated antibody to a final concentration of 1.0 μg/ml). Following an incubation of 1 h, the plates are washed, typically three times. A reaction solution, [100 μl, containing 167 μg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbancies at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

Comparative binding affinities of the mLL2, cLL2 and hcLL2 antibodies thus isolated may be determined by direct radioimmunoassay. mLL2 can be labeled with $^{131}$I or $^{125}$I using the chloramine T method (see, for example, Greenwood et al., *Biochem. J.*, 89: 123 (1963) which is incorporated by reference). The specific activity of the iodinated antibody is typically adjusted to about 10 μCi/μg. Unlabeled and labeled antibodies are diluted to the appropriate concentrations using reaction medium (HSFM supplemented with 1% horse serum and 100 μg/ml gentamicin). The appropriate concentrations of both labeled and unlabeled antibodies are added together to the reaction tubes in a total volume of 100 μl. A culture of Raji cells is sampled and the cell concentration determined. The culture is centrifuged and the collected cells washed once in reaction medium followed by resuspension in reaction medium to a final concentration of about 10⁷ cells/ml. All procedures are carried out in the cold at 4° C. The cell suspension, 100 μl, is added to the reaction tubes. The reaction is carried out at 4° C. for 2 h with periodic gentle shaking of the reaction tubes to resuspend the cells. Following the reaction period, 5 ml of wash buffer (PBS containing 1% BSA) is added to each tube. The suspension is centrifuged and the cell pellet washed a second time with another 5 ml of wash buffer. Following centrifugation, the amount of remaining radioactivity remaining in the cell pellet is determined in a gamma counter (Minaxi, Packard Instruments, Sterling, Va.).

The Raji cell surface antigen binding affinities of mix-and-match and fully humanized antibodies can be compared to that of cLL2 using various concentrations of mLL2 F(ab')₂ fragments devoid of the Fc portion as competitors, as evaluated by flow cytometry assay. Residual surface-bound LL2 antibodies carrying the human Fc portions (cLL2 and mix-and-match LL2) can be detected by a FITC-labeled anti-human Fc specific antibody in a flow cytometry assay. Where mix-and-match LL2 antibodies exhibit antigen-binding affinities similar to that of cLL2, it can be concluded that the original designs for the humanization of both the light and heavy chains retain the mLL2 immunoreactivity.

The internalization of mLL2, cLL2 and hLL2 antibodies into target cells can be followed by fluorescence labeling, essentially according to the procedure of Pirker et al., *J. Clin. Invest.*, 76: 1261 (1985), which is incorporated by reference. Cultured Raji cells are centrifuged and the cells resuspended in fresh medium to a concentration of about 5×10⁶ cells/ml. To each well of a 96-well microtiter plate, 100 μl of the cell suspension is added. The antibodies, 40 μg/ml, in a volume of 100 μl are added to the reaction wells at timed intervals so as to terminate all reactions simultaneously. The plate is incubated at 37° C. in a $CO_2$ cell culture incubator. Unbound antibodies are removed by washing the cells three times with cold 1% FCS/PBS at the end of the incubation. The cells are then treated with 1 ml of Formaid-Fresh [10% formalin solution (Fisher, Fair Lawn, N.J.)] for 15 min at 4° C. After washing, antibodies present either on the cell surface or inside the cells are detected by treatment with FITC-labeled goat anti-mouse antibody (Tago, Burlingame, Calif.), or FITC-labeled goat anti-human antibody (Jackson ImmunoResearch, West Grove, Pa.), depending on whether the antibody being assayed for is murine, chimeric, or humanized, respectively. Fluorescence distributions are evaluated using a BH-2 fluorescence microscope (Olympus, Lake Success, N.Y.).

The rate of antibody internalization can be determined according to Opresko et al., (*J. Biol. Chem.*, 262: 4116 (1987)), using radioiodinated antibody as tracer. Briefly, radiolabeled antibodies (1×10⁴ cpm) are incubated with the Raji cells (1×10⁶ cells/ml) at 4° C. for 2 h in 0.5 ml of DMEM medium containing 1% human serum. Following the reaction interval, non-specifically bound antibodies are removed by washing three times with 0.5 ml of DMEM medium. To each of the reaction tubes 0.5 ml of DMEM medium is added and the suspension incubated at 37° C. for the determination of internalization. At timed intervals, triplicates of cells are removed and chilled immediately in an ice bath to stop further internalization. Cells are centrifuged at 1000×g for 5 min at 4° C. The supernatant is removed and counted for radioactivity. The surface-bound radioactivity is removed by treatment with 1 ml 0.1 M acetate/0.1 M glycine buffer at pH 3.0 for 8 min. in the cold. Radioactivity removed by the acid treatment, and that remaining associated with the cells, are determined. The ratio of the $CPM_{internalization}/CPM_{surface}$ is plotted versus time to determine the rate of internalization from the slope.

Detailed protocols for oligonucleotide-directed mutagenesis and related techniques for mutagenesis of cloned DNA are well-known. For example, see Sambrook et al. and Ausubel et al. above.

Asn-linked glycosylation sites may be introduced into antibodies using conventional site-directed oligonucleotide mutagenesis reactions. For example, to introduce an Asn in position 18 of a kappa protein, one may alter codon 18 from AGG to AAC. To accomplish this, a single stranded DNA template containing the antibody light chain sequence is prepared from a suitable strain of *E. coli* (e.g., dut⁻ung-) in order to obtain a DNA molecule containing a small number of uracils in place of thymidine. Such a DNA template can be obtained by M13 cloning or by in vitro transcription using a SP6 promoter. See, for example, Ausubel et al., eds., CURRENT PROTOCOLS IN MOLECULAR BIOLOGY, John Wiley & Sons, NY, 1987. An oligonucleotide containing the mutated sequence is synthesized conventionally, annealed to the single-stranded template and the product treated with T4 DNA polymerase and T4 DNA ligase to produce a double-stranded DNA molecule. Transformation of wild type E. coli (dut+ung+) cells with the double-stranded DNA provides an efficient recovery of mutated DNA.

Alternatively, an Asn-linked glycosylation site can be introduced into an antibody light chain using an oligonucleotide containing the desired mutation as the primer and DNA clones of the variable regions for the VL chain, or by using RNA from cells that produce the antibody of interest as a template. Also see, Huse, in ANTIBODY ENGINEERING: A PRACTICAL GUIDE, Boerrebaeck, ed., W. H. Freeman & Co., pp 103–120, 1992. Site-directed mutagenesis can be performed, for example, using the TRANSFORMER™ kit (Clontech, Palo Alto, Calif.) according to the manufacturer's instructions.

Alternatively, a glycosylation site can be introduced by synthesizing an antibody chain with mutually priming oligonucleotides, one such containing the desired mutation. See, for example, Uhlmann, *Gene* 71: 29 (1988); Wosnick et al., Gene 60: 115 (1988); Ausubel et al., above, which are incorporated by reference.

Although the general description above referred to the introduction of an Asn glycosylation site in position 18 of the light chain of an antibody, it will occur to the skilled artisan that it is possible to introduce Asn-linked glycosylation sites elsewhere in the light chain, or even in the heavy chain variable region.

The representative embodiments described below are simply used to illustrate the invention. Those skilled in these arts will recognize that variations of the present materials fall within the broad generic scope of the claimed invention. The contents of all references mentioned herein are incorporated by reference.

EXAMPLE 1

Figure 2B:
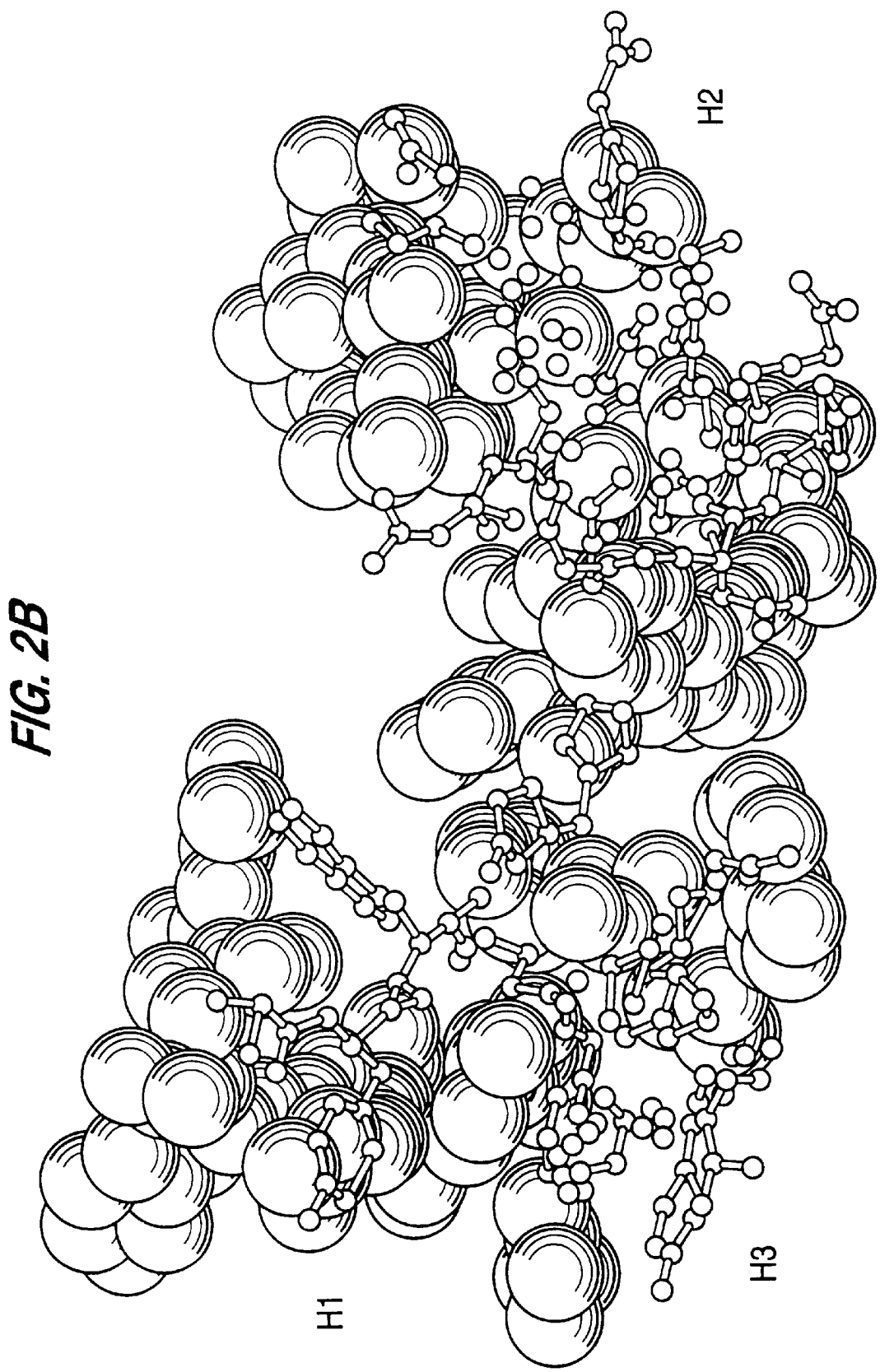

Choice of Human Frameworks and Sequence Design for the Humanization of LL2 Monoclonal Antibody By comparing the murine variable (V) region framework (FR) sequences of LL2 to that of human antibodies in the Kabat data base (Kabat et al., *Sequences of Proteins of Immunological Interest*, 5th ed., U.S. Department of Health and Human Services, U.S. Government Printing Office, Washington, D.C.), which is incorporated by reference, the human REI (FIG. 1A, Sequence ID No. 6) and EU (FIG. 1B, Sequence ID NOS. 9 and 8) sequences were found to exhibit the highest degree of sequence homology to the FRs of VK and VH domains of LL2, respectively. Therefore, the REI and EU FRs were selected as the human frameworks onto which the CDRs for LL2 VK and VH were grafted, respectively. The FR4 sequence of NEWM, however, rather than that of EU, was used to replace the EU FR4 sequence for the humanization of LL2 heavy chain. Based on the results of computer modeling studies (FIGS. 2A and 2B), murine FR residues having potential CDR contacts, which might affect the affinity and specificity of the resultant antibody, were retained in the design of the humanized FR sequences (FIG. 1).

Two versions of humanized heavy chain were constructed. In the first version (hLL2-1) (SEQ ID NO. 9), the glutamine (Q) at amino acid position 5 (Kabat numbering) was introduced to include a PstI restriction site to facilitate its subcloning into the staging vector (FIG. 3). This murine residue was converted, by oligo-directed mutagenesis, to the human EU residue valine (V) in hLL2-2 (SEQ ID NO. 8). It should be noted that in the original murine kappa chain variable sequence, a potential N-linked glycosylation site was identified at positions 18–20 (FIG. 1 SEQ ID NO. 2) and was used for carbohydrate addition. This glycosylation site was not included in the REI FR sequence used for LL2 light chain humanization.

See Example 3 for more oligonucleotide detail.

EXAMPLE 2

PCR Cloning and Sequence Elucidation for LL2 Heavy and Light Chain Variable Regions The variable regions for both heavy (VH) and light (VK) chains of mLL2 (IgG2a) were obtained by PCR cloning using DNA primers as described in general above and in greater detail in Example 3, below. As PCR is prone to mutations, the variable region sequence of multiple individual clones for either the heavy or light chains was determined for six clones and confirmed to be identical prior to use for the construction of the chimeric antibody.

Figure 3A:
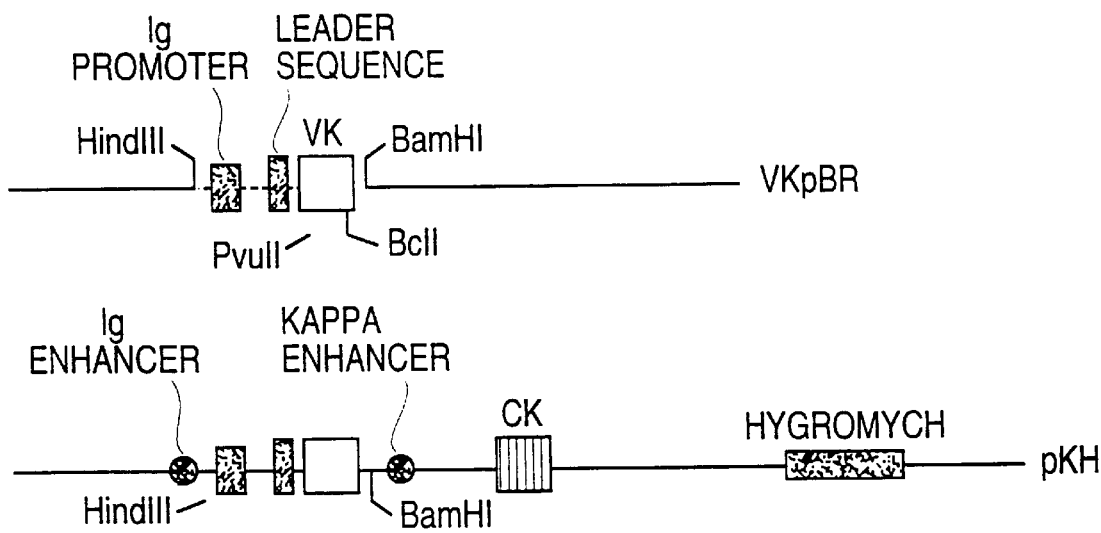
Figure 3B:
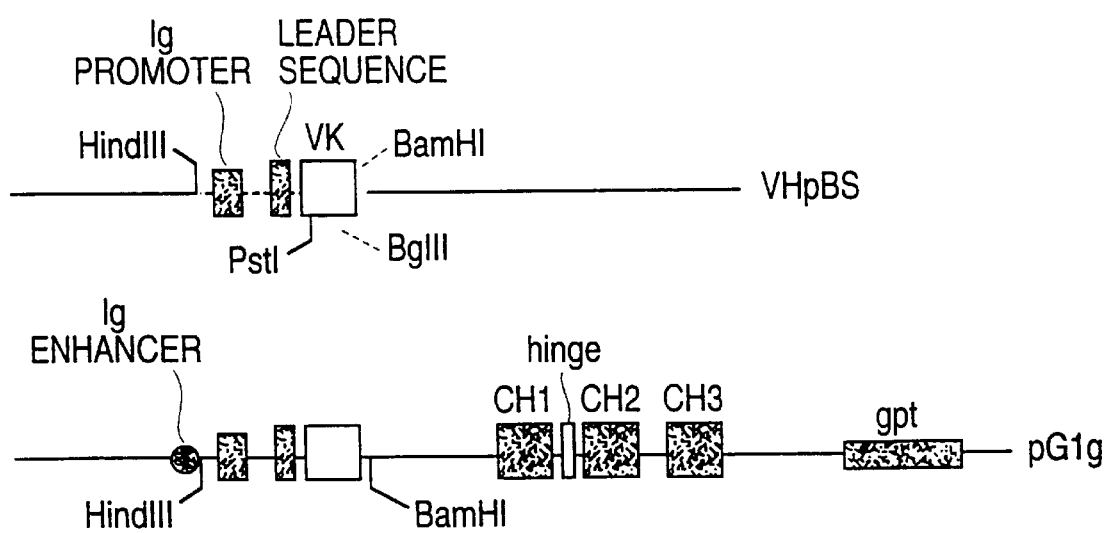
FIG. 3B shows the staging (VHpBS) and mammalian expression (pG1g) vectors.

The PCR products for VK were subcloned into a pBR327-based staging vector, VKp2R, which contained an Ig promoter, a signal peptide sequence and convenient restriction sites to facilitate in-frame ligation of the VK PCR products (FIG. 3A). The PCR products for VH were subcloned into a similar pBluescript-based staging vector, VHpBS (FIG. 3B).

As noted above, at least six individual clones containing the respective PCR products were sequenced according to the method of Sanger et al., 1977, above. All were shown to bear identical sequences and their respective sequences were elucidated, as shown in FIG. 4A for LL2 VK (Sequence ID NO. 1) and in FIG. 4B for LL2 VH (Sequence ID NO. 3). No defective mutations were identified within the sequences encoding the VK and VH regions. Comparison of the PCR-amplified variable region sequences of LL2 with the Kabat database (Kabat et al., above) suggested that the VK and VH sequences of LL2 belong to subgroup 5 and 2B, respectively. Important residues such as Cys for intra-domain disulfide linkage were retained at appropriate positions.

In the FR1 framework region of VK, an N-linked carbohydrate attachment site, Asu-Val-Thr, was identified at position 18–20 (FIG. 4A) (SEQ ID NO. 2), suggesting that the VK of LL2 might be glycosylated. As will be detailed below, SDS-PAGE analysis under reducing conditions demonstrated that this Asn glycosylation site is indeed utilized for carbohydrate addition. The presence of the glycosylation site in the variable region does not, however, appear to affect the immunoreactivity of the antibody. A comparison of the immunoreactivity of mLL2 with that of cLL2 in a competitive RIA showed that the two antibodies have nearly identical activities.

EXAMPLE 3

PCR/Gene Synthesis of the Humanized V Genes

Figure 6:
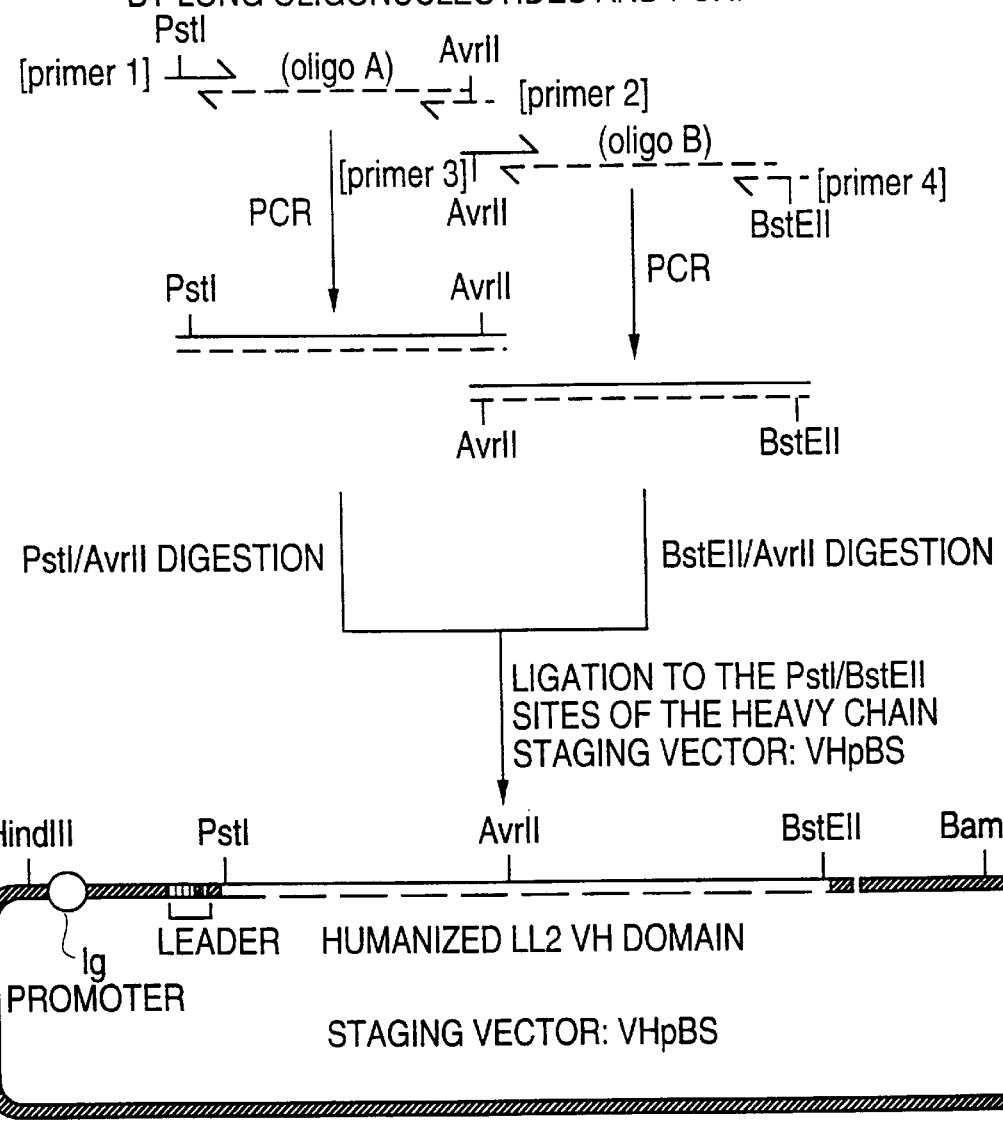
FIG. 6 is a schematic diagram representation of the PCR/gene synthesis of the humanized VH region and the subcloning into the staging vector, VHpBS.

The designed sequence for the hLL2 VH domain, the construction of the hLL2 VH domain by long oligonucleotides and PCR, and the staging vector VHpBS containing the hLL2 VH domain are summarized in the sketch shown in FIG. 6.

For the construction of the hLL2 VH domain, oligo A (149-mer) and oligo B (140-mer) were synthesized on an automated CYCLONE PLUS™ DNA synthesizer (Milligen Bioresearch).

Oligo A (Sequence ID No. 10 below) represents the minus strand of the hLL2 VH domain complementary to nt 24 to 172.

Sequence ID No. 10

5'-TAT AAT CAT TCC TAG GAT TAA TGT ATC CAA TCC ATT

CCA GAC CCT GTC CAG GTG CCT GCC TGA CCC AGT GCA

GCC AGT AGC TAG TAA AGG TGT AGC CAG AAG CCT TGC

AGG AGA CCT TCA CTG ATG ACC CAG GTT TCT TGA CTT

CAG CC-3'

Oligo B (Sequence ID No. 11 below) represents the minus strand of the hLL2 VH domain complementary to nt 180 to 320.

Sequence ID No. 11

5'-CCC CAG TAG AAC GTA GTA ATA TCC CTT CTT GCA CAA

AAA TAA AAT GCC GTG TCC TCA GAC CTC AGG CTG CTC

AGC TCC ATG TAG GCT GTA TTG GTG GAT TCG TCT GCA

GTT ATT GTG GCC TTG TCC TTG AAG TTC TGA TT-3'

Oligos A and B were cleaved from the support and deprotected by treatment with concentrated ammonium hydroxide. After the samples were vacuum-dried (SpeedVac, Savant, Farmingdale, N.Y.) and resuspended in 100 μl of water, incomplete oligomers (less than 100-mer) were removed by centrifugation through a CHROMOSPIN-100™ column (Clonetech, Palo Alto, Calif.) before the DNA oligomers were amplified by PCR. All flanking primers for the separate amplifications and PCR cloning of oligos A and B were purified by SDS-PAGE essentially according to the methods of Sambrook et al., 1989, above. From the CHROMASPIN-purified oligo A, 1 μl of sample stock was PCR-amplified in a reaction volume of 100 μl by adding 5 μl of 5 μM of oligo Sequence ID No. 12:

5'-CCA GCT GCA GCA ATC AGG GGC TGA AGT CAA GAA ACC

TG-3' and oligo Sequence ID No. 13:

5'-AAG TGG ATC CTA TAA TCA TTC CTA GGA TTA ATG-3' in the presence of 10 μl of 10× PCR Buffer (500 mM KCl, 100 mM Tris.HCL buffer, pH 8.3, 15 mM MgCl$_2$) and 5 units of AMPLITAQ™ DNA polymerase (Perkin Elmer Cetus, Norwalk, Conn.). This reaction mixture was subjected to 30 cycles of PCR reaction consisting of denaturation at 94° C. for 1 minute, annealing at 50° C. for 1.5 minutes, and polymerization at 72° C. for 1.5 minutes.

Oligo B was PCR-amplified by the primer pairs Sequence ID No. 14:

5'-TAA TCC TAG GAA TGA TTA TAC TGA GTA CAA TCA GAA

CTT CAA GGA CCA G-3' and Sequence ID No. 15:

5'-GGA GAC GGT GAC CGT GGT GCC TTG GCC CCA GTA GAA

CGT AGT AA-3' under similar conditions.

Double-stranded PCR-amplified products for oligos A and B were gel-purified, restriction-digested with PstI/AvrII (PCR product of oligo A) and BstEII/AvrII (PCR product of oligo B), and suclonned into the complementary PstI/BstEII sites of the heavy chain staging vector, VHpBS. The humanized VH sequence was subcloned into the pG1g vector, resulting in the final human IgG1 heavy chain expression vector, hLL2pG1g.

For constructing the full length DNA of the humanized VK sequence, oligo E (150-mer) and oligo F (121-mer) were synthesized as described above.

Oligo E Sequence ID No. 16:

5'-CCT AGT GGA TGC CCA GTA GAT CAG CAG TTT AGG TGC

TTT CCC TGG TTT CTG GTG GTA CCA GGC CAA GTA GTT

CTT CTG ATT TGC ACT GTA TAA AAC ACT TTG ACT GGA

CTT ACA GCT CAT AGT GAC CCT ATC TCC AAC AGA TGC

GCT CAG-3' represents the minus strand of the humanized VK domain complementary to nt 31 to 180, and this sequence was PCR-amplified by oligo Sequence ID No. 17:

5'-GAC AAG CTT CAG CTG ACC CAG TCT CCA TCA TCT CTG

AGC GCA TCT GTT GGA G-3' and oligo Sequence ID No. 18:

5'-AGA GAA TCG CGA AGG GAC ACC AGA TTC CCT AGT GGA

TGC CCA GTA-3'.

Oligo F Sequence ID No. 19:

5'-CCA GCT TGG TCC CTC CAC CGA ACG TCC ACG AGG AGA

GGT ATT GGT GAC AAT AAT ATG TTG CAA TGT CTT CTG

GTT GAA GAG AGC TGA TGG TGA AAG TAA AAT CTG TCC

CAG ATC CGC TGC C-3' represents the minus strand of the humanized LL2 VK domain complementary to nt 208 to 327, and was PCR amplified by oligo Sequence ID No. 17:

5'-GAC AAG CTT TCG CGA TTC TCT GGC AGC GGA TCT GGG

ACA G-3' and oligo Sequence ID No. 21:

5'-GAC CGG CAG ATC TGC ACC TTG GTC CCT CCA CCG-3'.

Gel-purified PCR products for oligos E and F were restriction-digested with PvuII/NruI and NruI/BglIII, respectively. The two PCR fragments E and F were then joined at the NruI site and ligated to the complementary PvuI/BclI sites of the light chain staging vector, VKpBR. The humanized VK sequence was subcloned into vector pKh to form the final human kappa chain expression vector, hLL2pKh.

To express the humanized antibodies, about 10 $\mu$g of linearized hLL2pKh and 20 $\mu$g of linearized hLL2pG1g were used to transfect $5\times10^6$ SP2/0 cells by electroporation. The transfectomas were selected with hygromycin at 500 $\mu$g/ml and secreted antibody was purified on a 1×3 cm column of protein A. After concentrating the purified antibody by Centricon 30 centifugation, antibody concentration was determined by ELISA. The final concentration of the antibody was adjusted to 1 mg/ml in PBS buffer containing 0.01% (w/v) sodium azide as a preservative.

In FIG. 1, there is compared the amino acid sequence between murine and humanized LL2 VK domains (FIG. 1A SEQ ID NOS. 2 and 6) and between murine and humanized LL2 VH domains (FIG. 1B SEQ ID NOS. 4, 9 and 8). In the VK chain, human REI framework sequences were used for all FRs. In the VH chain, human EU framework sequences were used for FR 1–3, and NEWM sequences were used for FR-4. Only human FR sequences that are different from that of the mouse are shown. Asterisks indicate murine FR sequences that are different from that of the human FR at corresponding positions. Murine residues at these positions were retained in the humanized structure. CDRs are boxed.

In FIG. 4A (Sequence ID NOS. 1 and 2) there are shown the double stranded DNA and corresponding amino acid sequences (shown by single letter code) of the murine LL2 VK domain. CDR 1–3 amino acid sequences are boxed. The corresponding display for VH is shown in FIG. 4B (Sequence ID NOS. 3 and 4).

In FIG. 5A (Sequence ID NOS. 5 and 6) and FIG. 5B (Sequence ID NOS. 7 and 8) there are shown double-stranded DNA sequences and amino acid sequences of humanized LL2 VK and LL2 VH, respectively. Amino acid sequences are shown by the single-letter code, and CDR amino acid sequences are boxed.

EXAMPLE 4

Construction, Expression and Purification of Chimeric LL2 Antibodies

The fragments containing the VK and VH sequences of LL2, together with the promoter and signal peptide sequences, were excised from LL2VKpBR and LL2VHpBS, respectively, by double restriction digestion with HindIII and BamHI. The about 600 bp VK fragments were then subcloned into the HindIII/BamHI site of a mammalian expression vector, pKh (FIG. 3A). pKh is a pSVhyg-based expression vector containing the genomic sequence of the human kappa constant region, an Ig enhancer, a kappa enhancer and the hygromycin-resistant gene. Similarly, the ca. 800 bp VH fragments were subcloned into the corresponding HindIII/BamHI site of pG1g (FIG. 3B), a pSVgpt-based expression vector carrying the genomic sequence of the human IgG1 constant region, an Ig enhancer and the xanthine-guanine phosphoribosyltransferase (gpt) gene. The final expression vectors are designated as LL2pKh and LL2pG1g, respectively.

The two plasmids were co-transfected into Sp2/0-Ag14 cells by electroporation and selected for hygromycin resistance. Supernatants from colonies surviving selection were monitored for chimeric antibody secretion by ELISA assay (see above). The transfection efficiency was approximately $1-10\times10^6$ cells. The antibody expression level, in a terminal culture, was found to vary in the range between <0.10 and 2.5 $\mu$g/ml.

Figure 7:
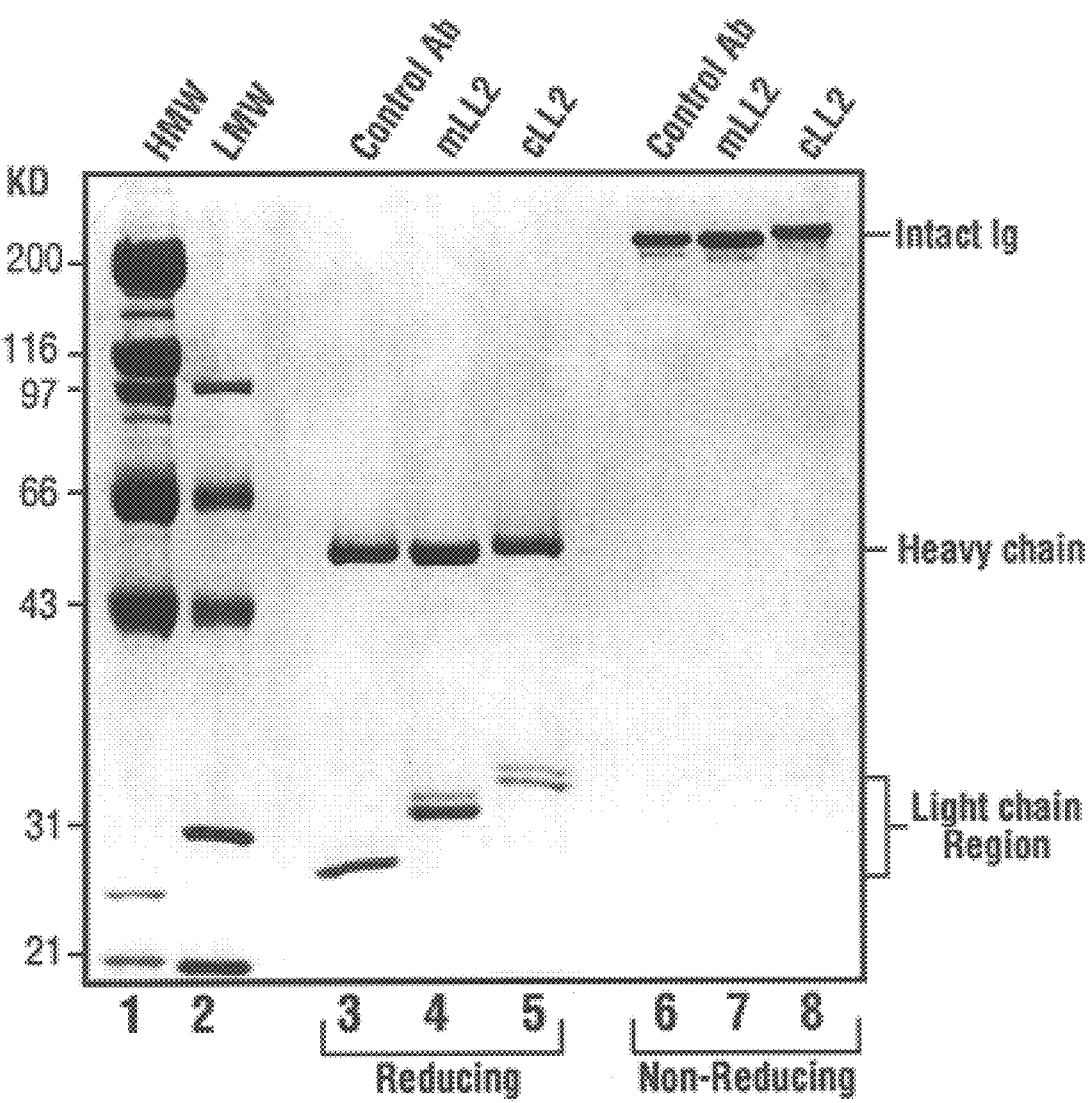
FIG. 7 shows SDS-PAGE analysis of mLL2 and cLL2 antibodies under non-reducing (lanes 6–8) and reducing (lanes 3–5, light and heavy chains) conditions. Lanes 3 and 6 include a control antibody.

FIG. 7 shows the results of analyzing protein A-purified mLL2 (lanes 4 and 7) and cLL2 (lanes 5 and 8) by SDS-PAGE under reducing and nonreducing conditions, respectively. HMW stands for high molecular weight protein markers, and LMW for light molecular weight markers. The light chains of both mLL2 and cLL2 (lanes 4 and 5) migrated primarily as a doublet band, with a higher than expected apparent molecular weight. As the human kappa constant region of cLL2 is known to contain no potential glycosylation site, it can be inferred that the potential glycosylation site identified in the FR1 region of LL2 VK domain was utilized.

Figure 8:
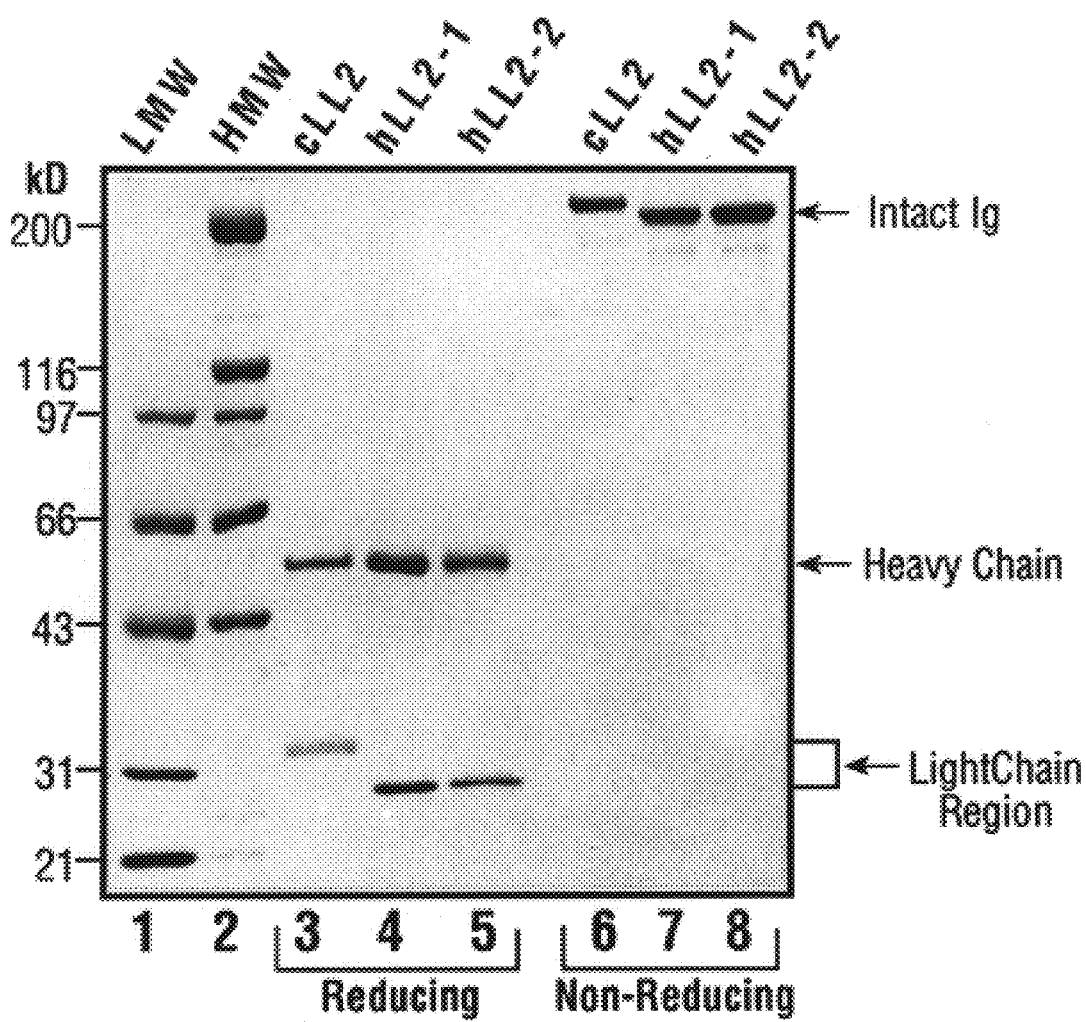
FIG. 8 shows SDS-PAGE analysis of different versions of cLL2 and hLL2 antibodies under reducing (lanes 3–5) and non-reducing (lanes 6–8) conditions.

FIG. 8 shows the results of analyzing different versions of hLL2 and cLL2 antibodies by SDS-PAGE under reducing and non-reducing conditions. As before, LMW and HMW are molecular weight markers. Lanes 3 and 6 are cLL2 antibodies. Lanes 4 and 7 are hLL2 with seven murine FR residues in the VH domain (hLL2-1). Lanes 5 and 8 are hLL2 with 6 murine FR residues in the VH domain (hLL2-2). The humanized light chains migrated more rapidly and as more discrete bands compared to chimeric light chains.

Figure 9:
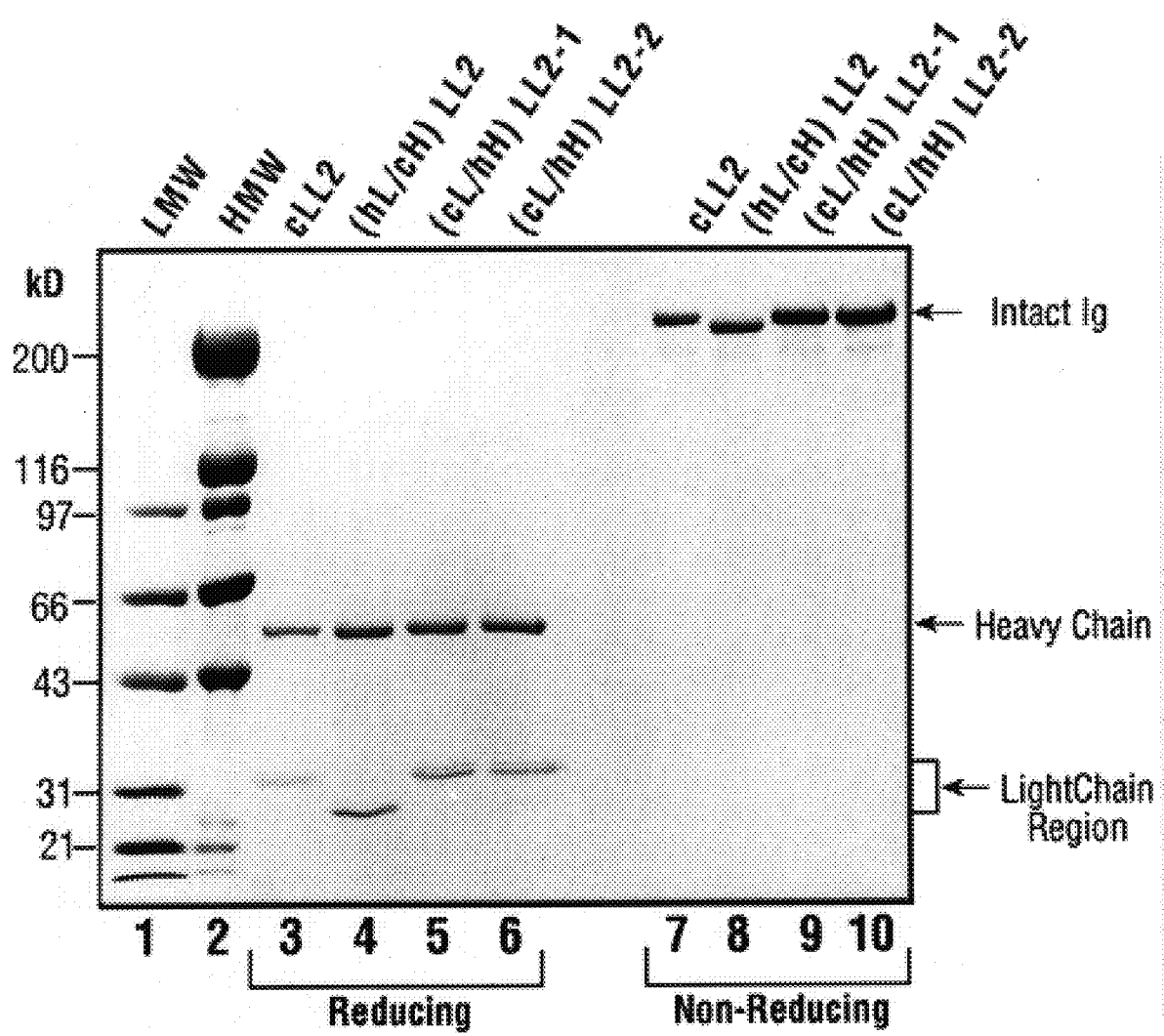
FIG. 9 shows SDS-PAGE analysis on mix-and-match cLL2 and hLL2 antibodies under reducing (lanes 3–6) and non-reducing (lanes 7–10) conditions. cLL2 serves as the control.

FIG. 9 shows the results of SDS-PAGE analysis on mix-and-match and cLL2 and hLL2 antibodies under both reducing and non-reducing conditions. Lanes 1 and 2 are molecular weight markers. Lanes 3 and 7 are cLL2. Lanes 4 and 8 are mix-and-match with a humanized light and chimeric heavy chain [(hL/cH)LL2]. Lanes 5 and 9 are chimeric light and humanized heavy (Version 1) chains [(cL/hH)LL2-1]. Lanes 6 and 10 are chimeric light and a humanized heavy (version 2) chains [(cL/hH)LL2-2]. The humanized LL2 version 1 contains 7 murine FR residues in the VH domain, while version 2 contains 6 murine FR residues in the VH domain. It is noteworthy that the position of the light chain of (hL/cH)LL2 (lane 4) is different from that of the others, suggesting that there is no carbohydrate attachment to the humanized LL2 light chain.

EXAMPLE 5

Binding of cLL2 Antibody to Raji Cell Surface Antigens

Figure 10:
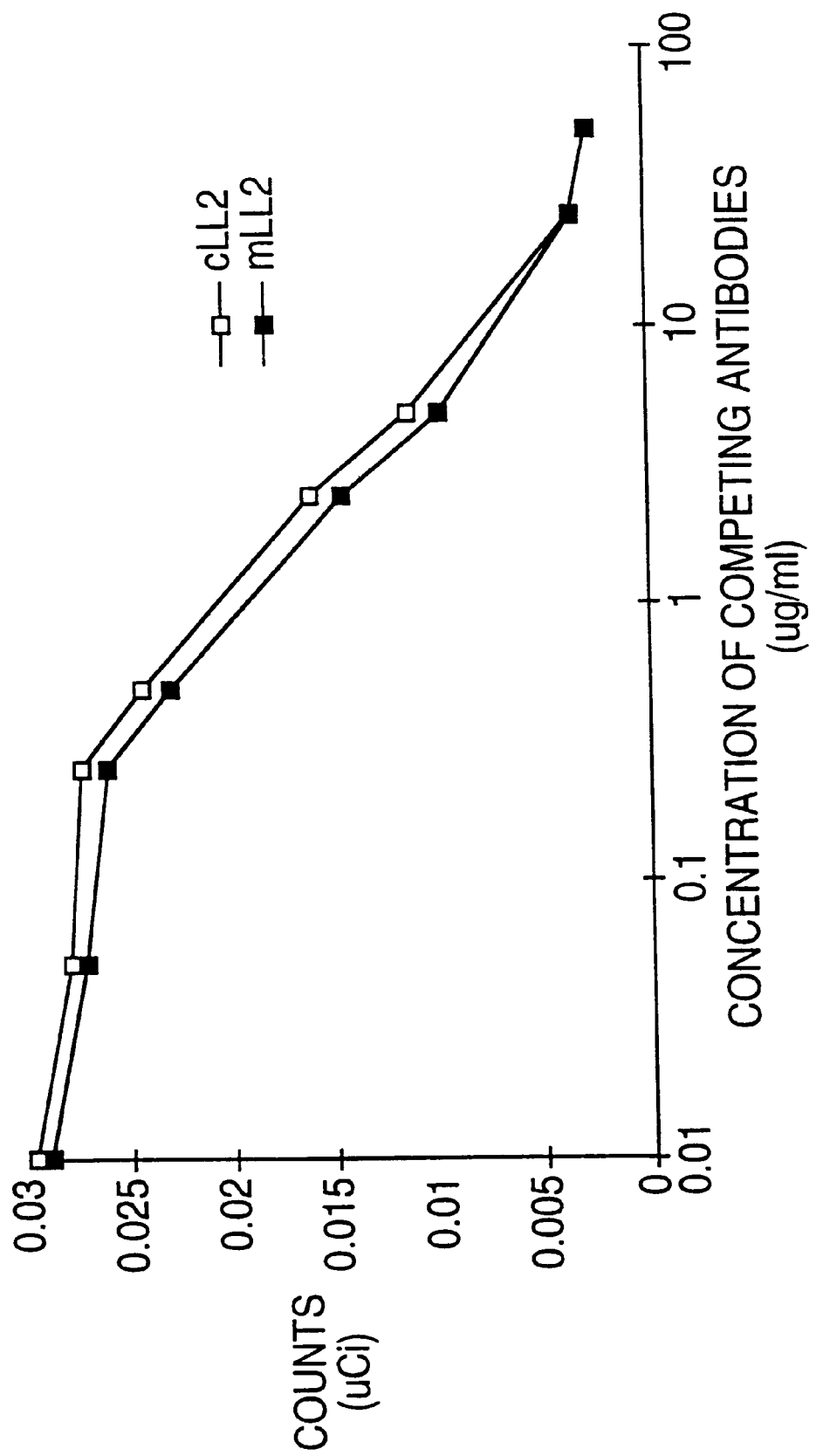
FIG. 10 shows the results of a comparative Raji cell competitive antibody binding assay involving mLL2 and cLL2 antibodies competing for binding to cells against tracer radiolabeled mLL2.

A competition cell binding assay was carried out to assess the immunoreactivity of cLL2 relative to the parent mLL2. Using $^{131}$I-labeled mLL2 (0.025 $\mu$g/ml) as a probe, Raji cells were incubated with the antibodies and the relative binding to the cells determined from the amount of cell-bound labeled mLL2 (see above). As shown by the competition assays described in FIG. 10, both mLL2 and cLL2 antibodies exhibited similar binding activities.

The results were confirmed by a second competition assay based on flow cytometry. Briefly, using Raji cells as before and varying the concentration of one antibody relative to other, as before, the amount of bound mLL2 or cLL2 was determined with FITC-labeled anti-mouse Fc or anti-human Fc antibodies followed by analysis using flow cytometry.

EXAMPLE 6

Binding of hLL2 Antibodies to Raji Cells

In experiments similar to those of Example 5, the antigen binding affinities of the three different combinations of mix-and-match or humanized LL2 were compared with that of cLL2 in the flow cytometry assay.

Briefly, 1 μg of cLL2, mix-and-match LL2, hLL2-1 or hLL2-2 antibodies were incubated with $10^8$ Raji cells in the presence of varying concentrations of mLL2 F(ab')$_2$ fragments (as competitor) in a final volume of 100 μl of PBS buffer supplemented with 1% FCS and 0.01% sodium azide. The mixture was incubated for 30 minutes at 4° C., and washed three times with PBS to remove unbound antibodies. By taking advantage of the presence of human Fc portions in the antibodies, the binding levels of the antibodies were assessed by adding a 20× diluted FITC-labeled goat anti-human IgG1, Fc fragment-specific antibodies (Jackson ImmunoResearch, West Grove, Pa.). The cells were washed three times with PBS, and fluorescence intensities measured by a FACSCAN fluorescence activated cell sorter (Becton-Dickinson, Bedford, Mass.). The results are shown in FIG. 11A.

Figure 11A:
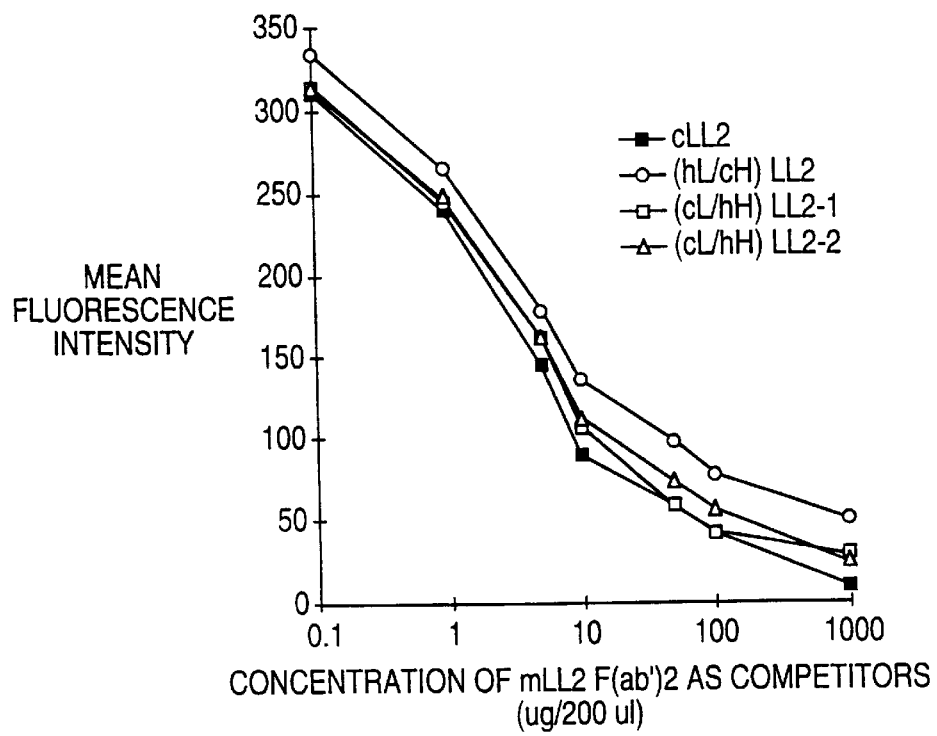
Figure 11B:
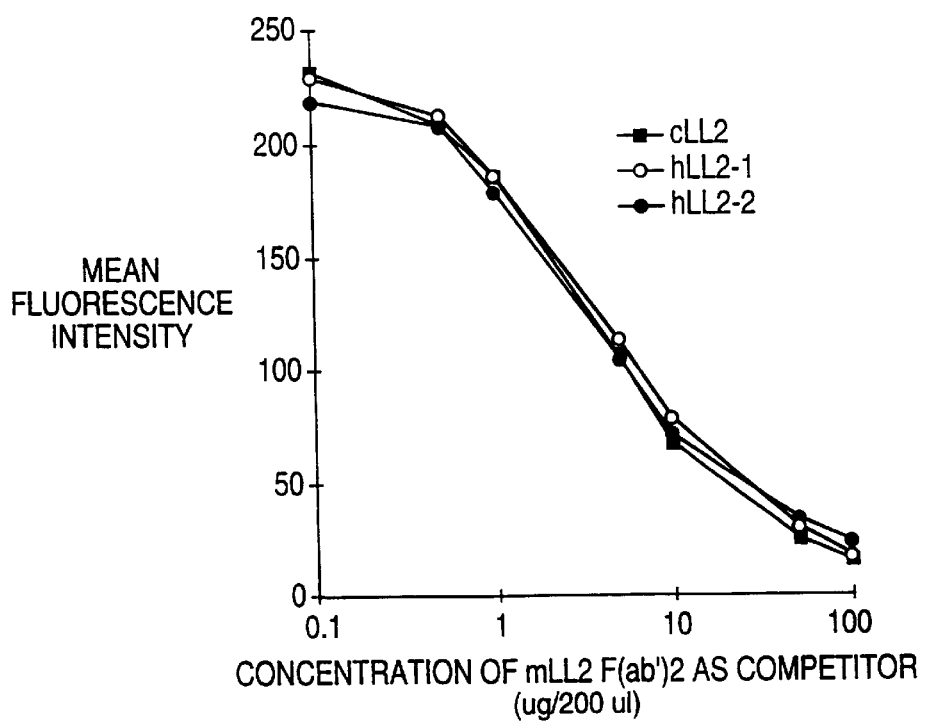
FIG. 11B shows a similar comparison with, and two versions of hLL2 compared to cLL2.

Using the same methods, cLL2 was compared to two versions of hLL2 (FIG. 11B).

The results shown in FIGS. 11A and B demonstrate that the immunoreactivity of cLL2 is similar or identical to that of humanized or mix-and-match antibodies. Taken together with the comparison of cLL2 with mLL2 (FIG. 10), the authenticity of the sequences for chimeric and humanized VK and VH obtained is established, and the functionality of cLL2 and hLL2 confirmed.

EXAMPLE 7

Internalization of mLL2 and cLL2 by Raji Cells

One of the unique characteristics of the LL2 antibody is its rapid internalization upon binding to Raji cells (Shih et al., 1994 above). Murine LL2 after internalization is likely to be rapidly transferred to the Golgi apparatus and from there to the lysosomes, the organelle responsible for the degradation of a wide variety of biochemicals (Keisari et al., *Immunochem.*, 10: 565 (1973)).

Rates of antibody internalization were determined according to Opresko et al., 1987 above. The ratieo of $CPM_{intracellular}/CPM_{surface}$ was determined as a function of time.

Rates of LL2 antibody internalization were determined by incubating radiolabeled LL2 antibody ($1 \times 10^6$ cpm) with $0.5 \times 10^6$ Raji cells in 0.5 ml of DMEM buffer containing 1% human serum for 2 hrs. at 4° C. Excess human serum was included to saturate Raji cell surface Fc receptors in order to exclude or minimize non-antigen-specific internalization mediated through the Fc receptors. Unbound radiolabeled LL2 antibodies were removed from the cells by washing three times with 0.5 ml portions of DMEM at 4° C. Cells were then incubated at 37° C., and, at timed intervals, aliquots of the cell suspension were transferred to ice in order to stop internalization. The cells in these aliquots were isolated by centrifugation at 1,000×g for 5 mins. at 4° C., and surface bound radiolabeled LL2 stripped off cells with 1 ml of 0.1 M glycine acetate buffer, pH 3, for 8 mins. at 4° C. Radioactivity thus obtained (CPM surface) and radioactivity remaining in the cells (CPM intracellular) were determined. Rates of internalization were calculated from the slope of the plot of intracellular:surface radioactivity ratios as a function of time.

Figure 12:
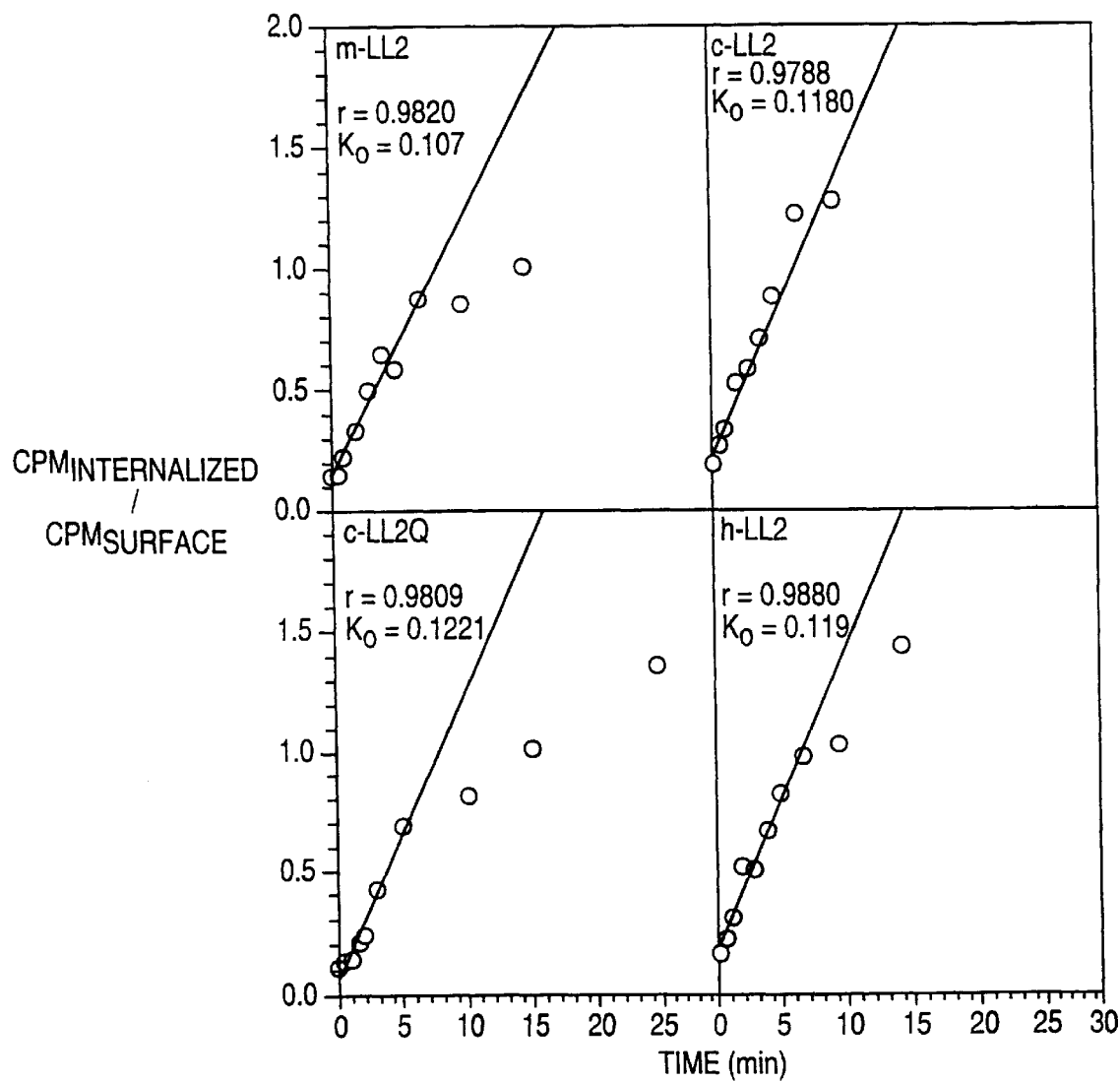
FIG. 12 shows a comparison of antibody internalization-:surface binding ratios as a function of time for cLL2, cLL2 (Q to V mutagenesis), hLL2 and mLL2 antibodies.

As shown in FIG. 12, mLL2, cLL2, cLL2Q and hLL2 antibodies were internalized at a similar rate (Ke=0.107 (mLL2) to 0.1221 (cLL2Q, NVT to QVT mutation). Those numbers suggested that approximately 50% of the surface-bound antibody could be internalized in 10 min. The results show that neither chimerization nor humanization nor deglycosylation by mutagenesis of mLL2 antibodies impair rates of internalization.

The pattern of internalization for mLL2, cLL2 and hLL2 was also monitored by fluorescence microscopy on a time-course basis using a FITC-labeled second antibody probe as described in the specification. Internalization of both antibodies was observed in at the earliest time point measurable. At 5 minutes, antibodies were seen both on the cell surface and internalized in areas immediately adjacent to the membrane as cytoplasmic micro-vesicles. At 15 min. post-incubation, the fine dots dispersed around the intramembrane began to merge into a group of granules, at locations believed to be the Golgi apparatus. As more antibodies were being internalized after 30 min. of incubation, redistribution of the grouped antibodies to scattered locations, probably the lysosomes in which the antibodies were degraded, was observed. At 2 hrs post-incubation, most of the antibodies were found inside the cell. Only strong surface staining was observed when LL2 was incubated for 20 min on ice. Both mLL2 and cLL2 were internalized with a similar pattern. The internalization of LL2 was associated specifically with antigen-antibody binding, as the irrelevant control humanized antibody demonstrated only dull surface staining.

A103 antibody (an IgG2a antibody that binds to the surface of all human epithelial cells but does not internalize efficiently (Mattes et al., *Hybridoma*, 2: 253 (1983)) showed strong membrane staining at up to 2 h, while the anti-transferrin receptor antibody (5F9) internalized rapidly, just as did LL2.

EXAMPLE 8

Role of Glycosylation Site in FR1 Region of LL2 VK Sequence

Of particular inventive interest is the identification of an Asn-glycosylation site at position 18–20 within the FR1 region of the LL2 NVT light chain sequence (FIG. 4A SEQ ID NO. 2). As shown above, SDS-PAGE analysis under reducing condition suggests that the Asn glycosylation site is utilized for carbohydrate addition.

In this example, the influence of the carbohydrate moiety at position 18–20 on the functional activities of the light chains was examined.

Figure 13:
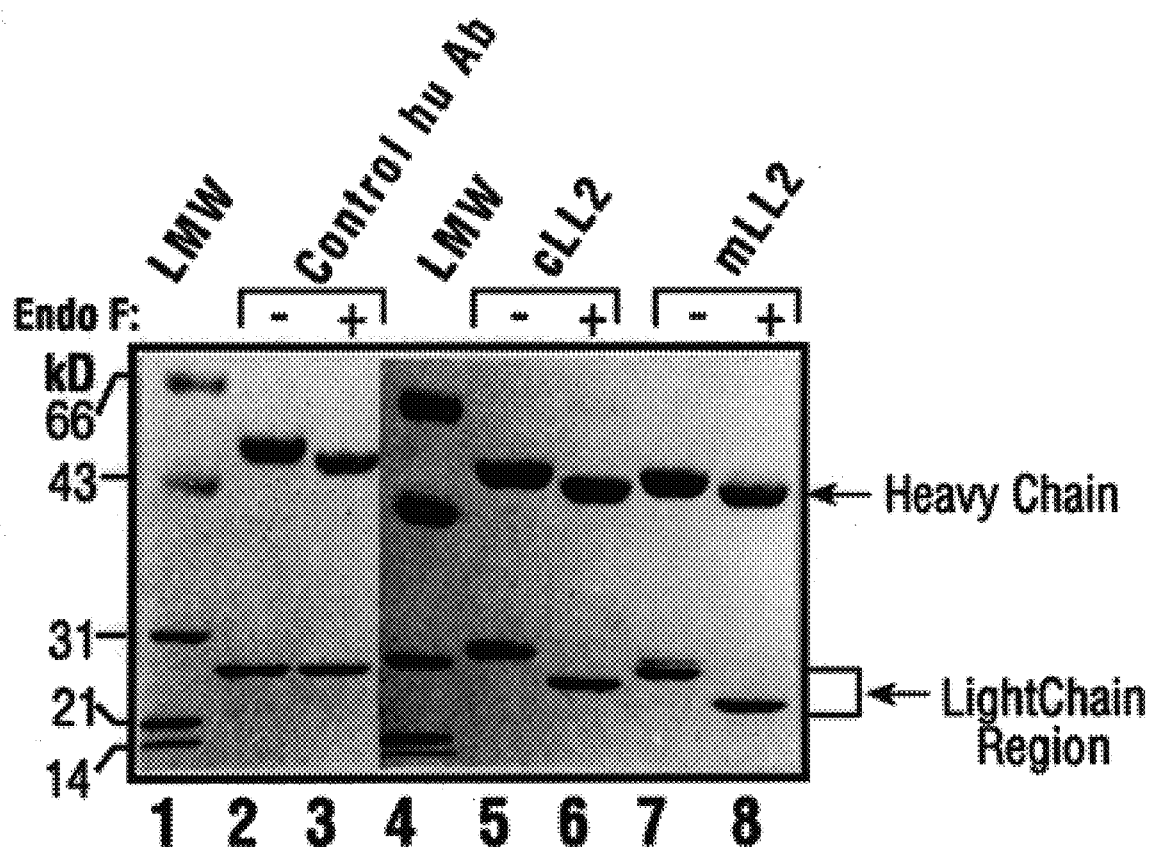
FIG. 13 shows an SDS-PAGE analysis of mLL2 and cLL2 after deglycosylation by endoglycosidase F.

Murine and chimeric LL2 light chains were treated with (+) or without (−) endoglycosidase F conventionally, and the antibody products examined by SDS-PAGE under reducing and non-reducing conditions (FIG. 13). There was no distinction between the antibody types as to electrophoretic behavior. In both cases, deglycosylation reduced the rate of migration of the light chain.

The effect of deglycosylation on the binding affinity to Raji cells of the mLL2 antibody is shown in FIG. 14. Removing carbohydrate by endoglycosidase F was without influence on the binding activity.

A mutation was introduced at position 18 of the light chain so that the Asn was replaced with Gln to produce LL2Q VK FR1. SDS-PAGE analyses demonstrated that the NVT to QVT mutation abolished glycosylation of the antibody. Comparison of the Raji cell binding affinity for cLL2 with and without light chain VK glycosylation demonstrated that the carbohydrate moiety was without influence on binding of the antibody to these cells.

It can be concluded that the presence of the carbohydrate site in the variable region does not affect the immunoreactivity of the antibody. Computer modeling studies suggested that the VK carbohydrate moiety in LL2 is remotely positioned from the CDRs and forms a "cap" over the bottom loops of the FR-associated β-barrels supporting the CDRs.

Humanization without inclusion of the original glycosylation site resulted in a CDR-grafted LL2 antibody with immunoreactivity comparable to that of its murine counterpart.

These characteristics indicate that the glycosylation site can be used for conjugating therapeutic or diagnostic agents to LL2 without compromising the ability of the antibody to bind and internalize in B-lymphoma or leukemia cells.

EXAMPLE 9

Conjugation of LL2 at its Carbohydrate-bearing Site

The apparent lack of involvement of the variable region carbohydrate moiety in the functional activities of mLL2, cLL2 and hLL2 mabs indicates that this moiety could profitably be used as the site of attachment of cytotoxic or detection agents such as radionuclides or toxins, and thereby avoid potential interference with the binding of the conjugate to a cell surface.

Using procedures described in Shih et al., U.S. Pat. No. 5,057,313 (which is incorporated by reference) for preparing antibody conjugates through an oxidized carbohydrate moiety of the antibody and a primary alkylamino group of a polymeric carrier to which are covalently one or more of a variety of drugs, toxins, chelators and detectable labels, a doxorubicin-dextran-LL2 antibody fragment devoid of appended glycans was produced containing multiple copies of the drug. The carbohydrate moieties of the cLL2 VK FR1region involved were those covalently bound to the Asn glycosylation site.

In one synthesis, dextran (18–40 kDa) was converted to an amino dextran by oxidation of the dextran by $NaIO_4$, Schiff base formation with $NH_2$—$CH_2$—$CHOH$—$CH_2$—$NH_2$, and reduction with $NaBH_4$. The amino dextran was then condensed with doxorubicin (DOX) in the presence of succinic anhydride and 1-ethyl-3-(3-dimethylaminopropyl) carbodiimide to produce DOX-aminodextran. The latter was then condensed with an aldehydic group on LL2 VK FR-1 produced by oxidizing the carbohydrate moiety of the antibody fragment with $NaIO_4$.

In one preparation of DOX-LL2, the number of moles of DOX attached to dextran was 14 moles per mole dextran, and the number of moles of doxorubicin per mole F(ab')2 was 8.9. The immunoreactivity in the Raji cell binding assay above was about 80% of control values.

This conjugation system is not limited to the mLL2 antibody. In a comparative study, 15–19 moles of DOX/mole of cLL2 were bound.

The conjugation possibilities are not limited to the use of a carrier dextran as in the example above. For example, the carbohydrate moiety of the LL2 VK FR1 region can be oxidized to produce aldehydic groups. These in turn can be reacted with an amino group on any drug to produce a Schiff base which, upon reduction, produces multiple copies of the drug stably linked to the antibody via alkyamine groups.

For example, where the drug is aminohexyl DTPA (a chelating agent), there is produced a LL2 covalently bound to a chelator. The chelator can be used to deliver to target tissues, for example, a radionuclide or paramagnetic metal ion, with a potential for diagnostic and therapeutic uses. DTPA-LL2 conjugates were produced containing 5.5 moles of the chelator/mole of antibody which, in turn, chelated 47.3% of Y-90 and 97.4% In-111.

It should be emphasized that the above-described examples merely describe several specific embodiments of the invention, and applicants do not intend to be limited as to scope of claims by these specific examples.

Applicants also incorporate by reference all publications and patents cited in the specification.

---

We claim:

1. A humanized LL2 (hLL2) monoclonal antibody (mAb) or fragment thereof comprising the complementarity-determining regions (CDRs) of mouse LL2 (mLL2) and the framework (FR) regions of the light and heavy chain variable regions of a human antibody and the light and heavy chain constant regions of a human antibody, wherein said hLL2 mAb or fragment thereof retains substantially the B-lymphoma cell and leukemia cell targeting and cell internalization characteristics of said mLL2 mAb, and wherein said hLL2 mAb or fragment thereof is less immunogenic in a human subject than is said mLL2 mAb, wherein the CDRs of the light chain variable region of mLL2 comprise CDR1 comprising amino acids 24 to 40 of SEQ ID NO: 2, CDR2 comprising amino acids 56 to 62 of SEQ ID NO: 2 and CDR3 comprising 95 to 103 of SEQ ID NO: 2 and the CDRs of the heavy chain variable region of mLL2 comprise CDR1 comprising amino acids 31 to 35 of SEQ ID NO: 4, CDR2 comprising amino acids 50 to 66 of SEQ ID NO: 4 and CDR3 comprising 99 to 105 of SEQ ID NO: 4.

2. The hLL2 mAb or fragment thereof according to claim 1, wherein said fragment is selected from the group consisting of F(ab')$_2$, Fab', Fab and Fv.

3. The hLL2 mAb or fragment thereof according to claim 1, wherein said fragment is a fragment of a hLL2 mAb comprising the heavy chain variable region of SEQ ID NO: 8 and the light chain variable region of SEQ ID NO: 6.

4. The hLL2 mAb or fragment thereof according to claim 1, wherein said fragment is a fragment of a hLL2 mAb comprising the heavy chain variable region of SEQ ID NO: 9 and the light chain variable region of SEQ ID NO: 6.

5. A B-lymphoma cell and leukemia cell targeting diagnostic or therapeutic conjugate, comprising a hLL2 mAb or fragment thereof according to claim 1 that binds to said cells, wherein said hLL2 mAb or fragment thereof is bound to a diagnostic or therapeutic agent.

6. A diagnostic conjugate according to claim 5, wherein said diagnostic agent comprises a label.

7. A method of diagnosing a B-cell lymphoma cell or leukemia cell in a subject, comprising the step of administering to said subject a diagnostically effective amount of a diagnostic conjugate according to claim 6, formulated in a pharmaceutically acceptable vehicle, and detecting said label.

8. A therapeutic conjugate according to claim 5, wherein said therapeutic agent comprises a cytotoxic agent.

9. A therapeutic conjugate according to claim 8, wherein said cytotoxic agent is a toxin.

10. A conjugate according to claim 5, wherein said agent is bound to said mAb or fragment thereof, by means of a carbohydrate moiety of said mAb or fragment thereof.

11. A method of treating a B-cell lymphoma cell or leukemia cell in a subject, comprising the step of administering to said subject a therapeutically effective amount of a therapeutic conjugate according to claim 5, formulated in a pharmaceutically acceptable vehicle.

12. A DNA sequence encoding the hLL2 mAb or fragment thereof according to claim 1.

13. An expression vector comprising the DNA sequence according to claim 12.

14. The expression vector according to claim 13, wherein said vector further comprises an Ig promoter, a DNA sequence encoding a signal peptide, a genomic sequence encoding a human IgG1 heavy chain constant region, an Ig enhancer and at least one DNA sequence encoding a marker.

15. A method for the expression of a hLL2 monoclonal antibody or fragment thereof according to claim 1, comprising:

(a) linearizing at least one expression vector comprising a DNA sequence encoding a hLL2 mAb or fragment thereof;

(b) transfecting mammalian cells with said at least one linearized vector;

(c) selecting said transfected cells which express a marker gene; and (d) selecting cells secreting said hLL2 mAb or fragment thereof from said cells which express said marker gene.

16. A chimeric LL2 (cLL2) monoclonal antibody, (mAb) or fragment thereof comprising the light and heavy chain variable regions of mouse LL2 (mLL2) and the light and heavy chain constant regions of a human antibody, wherein said cLL2 mAb retains substantially the B-lymphoma cell and leukemia cell targeting and cell internalization characteristics of said mLL2 mAb, and wherein said cLL2 mAb is less immunogenic in a human subject than is said mLL2 mAb, wherein said cLL2 comprises the light chain variable region of SEQ ID NO: 2 and the heavy chain variable region of SEQ ID NO: 4.

17. The cLL2 mAb or fragment thereof according to claim 16, wherein said fragment is selected from the group consisting of F(ab')$_2$, Fab' and Fab.

18. A B-lymphoma cell and leukemia cell targeting diagnostic or therapeutic conjugate, comprising a cLL2 mAb or fragment thereof according to claim 16 that binds to said cells, wherein said cLL2 mAb or fragment thereof is bound to a diagnostic or therapeutic agent.

19. A diagnostic conjugate according to claim 18, wherein said diagnostic agent comprises a label.

20. A method of diagnosing a B-cell lymphoma cell or leukemia cell in a subject, comprising the step of administering to said subject a diagnostically effective amount of a diagnostic conjugate according to claim 19, formulated in a pharmaceutically acceptable vehicle, and detecting said label.

21. A therapeutic conjugate according to claim 18, wherein said therapeutic agent comprises a cytotoxic agent.

22. A therapeutic conjugate according to claim 21, wherein said cytotoxic agent is a toxin.

23. A conjugate according to claim 18, wherein said agent is bound to said mAb, or fragment thereof, by means of a carbohydrate moiety of said mAb or fragment thereof.

24. A method of treating a B-cell lymphoma cell or leukemia cell in a subject, comprising the step of administering to said subject a therapeutically effective amount of a therapeutic conjugate according to claim 18, formulated in a pharmaceutically acceptable vehicle.

25. A DNA sequence encoding the cLL2 mAb or fragment thereof according to claim 16.

26. An expression vector comprising the DNA sequence according to claim 25.

27. The expression vector according to claim 26, wherein said vector further comprises an Ig promoter, a DNA sequence encoding a signal peptide, a genomic sequence encoding a human IgG1 heavy chain constant region, an Ig enhancer and at least one DNA sequence encoding a marker.

28. A method for the expression of a cLL2 monoclonal antibody or fragment thereof according to claim 16, comprising:

(a) linearizing at least one expression vector comprising a DNA sequence encoding a cLL2 mAb or fragment thereof;

(b) transfecting mammalian cells with said at least one linearized vector;

(c) selecting said transfected cells which express a marker gene; and (d) selecting cells secreting said cLL2 mAb or fragment thereof from said cells which express said marker gene.

29. The cLL2 mAb and fragments thereof according to claim 16, wherein amino acid 18 of SEQ ID NO: 2 is changed from an asparagine to a glutamine.

30. The cLL2 mAb and fragments thereof according to claim 29, wherein said fragments are selected from the group consisting of F(ab')$_2$, Fab' and Fab.

31. A B-lymphoma cell and leukemia cell targeting conjugate, comprising a cLL2 mAb or fragment thereof according to claim 29 or a specific binding fragment thereof that binds to said cells, wherein said cLL2 mAb or said specific binding fragment thereof is bound to a diagnostic or therapeutic reagent.

32. A method of treating a B-cell lymphoma cell or leukemia cell in a subject, comprising the step of administering to said subject a therapeutically effective amount of the conjugate according to claim 31, formulated in a pharmaceutically acceptable vehicle.

33. A method of diagnosing a B-cell lymphoma cell or leukemia cell in a subject, comprising the step of administering to said subject a diagnostically effective amount of the conjugate according to claim 31, formulated in a pharmaceutically acceptable vehicle, and detecting said label.

34. A DNA sequence encoding the cLL2 mAb or fragment thereof according to claim 29.

\* \* \* \* \*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 339 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..339

(xi) SEQUENCE DESCRIPTION: SEQ ID NO:1:

```
GAC ATT CAG CTG ACC CAG TCT CCA TCA TCT CTG GCT GTG TCT GCA GGA        48
Asp Ile Gln Leu Thr Gln Ser Pro Ser Ser Leu Ala Val Ser Ala Gly
 1               5                  10                  15

GAA AAC GTC ACT ATG AGC TGT AAG TCC AGT CAA AGT GTT TTA TAC AGT        96
Glu Asn Val Thr Met Ser Cys Lys Ser Ser Gln Ser Val Leu Tyr Ser
             20                  25                  30
```

```
GCA AAT CAC AAG AAC TAC TTG GCC TGG TAC CAG CAG AAA CCA GGG CAG      144
Ala Asn His Lys Asn Tyr Leu Ala Trp Tyr Gln Gln Lys Pro Gly Gln
        35                  40                  45

TCT CCT AAA CTG CTG ATC TAC TGG GCA TCC ACT AGG GAA TCT GGT GTC      192
Ser Pro Lys Leu Leu Ile Tyr Trp Ala Ser Thr Arg Glu Ser Gly Val
 50                  55                  60

CCT GAT CGC TTC ACA GGC AGC GGA TCT GGG ACA GAT TTT ACT CTT ACC      240
Pro Asp Arg Phe Thr Gly Ser Gly Ser Gly Thr Asp Phe Thr Leu Thr
 65                  70                  75                  80

ATC AGC AGA GTA CAA GTT GAA GAC CTG GCA ATT TAT TAT TGT CAC CAA      288
Ile Ser Arg Val Gln Val Glu Asp Leu Ala Ile Tyr Tyr Cys His Gln
                 85                  90                  95

TAC CTC TCC TCG TGG ACG TTC GGT GGA GGG ACC AAG CTG GAG ATC AAA      336
Tyr Leu Ser Ser Trp Thr Phe Gly Gly Gly Thr Lys Leu Glu Ile Lys
            100                 105                 110

CGT                                                                  339
Arg
```

(2) INFORMATION FOR SEQ ID NO:2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:2:

```
Asp Ile Gln Leu Thr Gln Ser Pro Ser Ser Leu Ala Val Ser Ala Gly
 1               5                  10                  15

Glu Asn Val Thr Met Ser Cys Lys Ser Gln Ser Val Leu Tyr Ser
             20                  25                  30

Ala Asn His Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Arg Val Gln Val Glu Asp Leu Ala Ile Tyr Tyr Cys His Gln
                 85                  90                  95

Tyr Leu Ser Ser Trp Thr Phe Gly Gly Gly Thr Lys Leu Glu Ile Lys
            100                 105                 110

Arg
```

(2) INFORMATION FOR SEQ ID NO:3:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..348

(xi) SEQUENCE DESCRIPTION: SEQ ID NO:3:

```
CAG GTC CAG CTG CAG GAG TCA GGG GCT GAA CTG TCA AAA CCT GGG GCC       48
Gln Val Gln Leu Gln Glu Ser Gly Ala Glu Leu Ser Lys Pro Gly Ala
 1               5                  10                  15

TCA GTG AAG ATG TCC TGC AAG GCT TCT GGC TAC ACC TTT ACT AGC TAC       96
Ser Val Lys Met Ser Cys Lys Ala Ser Gly Tyr Thr Phe Thr Ser Tyr
```

```
                  20                  25                  30
TGG CTG CAC TGG ATA AAA CAG AGG CCT GGA CAG GGT CTG GAA TGG ATT      144
Trp Leu His Trp Ile Lys Gln Arg Pro Gly Gln Gly Leu Glu Trp Ile
        35                  40                  45

GGA TAC ATT AAT CCT AGG AAT GAT TAT ACT GAG TAC AAT CAG AAC TTC      192
Gly Tyr Ile Asn Pro Arg Asn Asp Tyr Thr Glu Tyr Asn Gln Asn Phe
 50                  55                  60

AAG GAC AAG GCC ACA TTG ACT GCA GAC AAA TCC TCC AGC ACA GCC TAC      240
Lys Asp Lys Ala Thr Leu Thr Ala Asp Lys Ser Ser Ser Thr Ala Tyr
 65                  70                  75                  80

ATG CAA CTG AGC AGC CTG ACA TCT GAG GAC TCT GCA GTC TAT TAC TGT      288
Met Gln Leu Ser Ser Leu Thr Ser Glu Asp Ser Ala Val Tyr Tyr Cys
                 85                  90                  95

GCA AGA AGG GAT ATT ACT ACG TTC TAC TGG GGC CAA GGC ACC ACT CTC      336
Ala Arg Arg Asp Ile Thr Thr Phe Tyr Trp Gly Gln Gly Thr Thr Leu
                100                 105                 110

ACA GTC TCC TCG                                                      348
Thr Val Ser Ser
        115

(2) INFORMATION FOR SEQ ID NO:4:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:4:

Gln Val Gln Leu Gln Glu Ser Gly Ala Glu Leu Ser Lys Pro Gly Ala
 1               5                  10                  15

Ser Val Lys Met Ser Cys Lys Ala Ser Gly Tyr Thr Phe Thr Ser Tyr
                 20                  25                  30

Trp Leu His Trp Ile Lys Gln Arg Pro Gly Gln Gly Leu Glu Trp Ile
        35                  40                  45

Gly Tyr Ile Asn Pro Arg Asn Asp Tyr Thr Glu Tyr Asn Gln Asn Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Asp Ile Thr Thr Phe Tyr Trp Gly Gln Gly Thr Thr Leu
                100                 105                 110

Thr Val Ser Ser
        115

(2) INFORMATION FOR SEQ ID NO:5:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..339

(xi) SEQUENCE DESCRIPTION: SEQ ID NO:5:

GAC ATT CAG CTG ACC CAG TCT CCA TCA TCT CTG AGC GCA TCT GTT GGA       48
Asp Ile Gln Leu Thr Gln Ser Pro Ser Ser Leu Ser Ala Ser Val Gly
```

```
                1               5                    10                   15
GAT AGG GTC ACT ATG AGC TGT AAG TCC AGT CAA AGT GTT TTA TAC AGT           96
Asp Arg Val Thr Met Ser Cys Lys Ser Ser Gln Ser Val Leu Tyr Ser
                        20                  25                  30

GCA AAT CAC AAG AAC TAC TTG GCC TGG TAC CAG CAG AAA CCA GGG AAA          144
Ala Asn His Lys Asn Tyr Leu Ala Trp Tyr Gln Gln Lys Pro Gly Lys
            35                  40                  45

GCA CCT AAA CTG CTG ATC TAC TGG GCA TCC ACT AGG GAA TCT GGT GTC          192
Ala Pro Lys Leu Leu Ile Tyr Trp Ala Ser Thr Arg Glu Ser Gly Val
        50                  55                  60

CCT TCG CGA TTC TCT GGC AGC GGA TCT GGG ACA GAT TTT ACT TTC ACC          240
Pro Ser Arg Phe Ser Gly Ser Gly Ser Gly Thr Asp Phe Thr Phe Thr
65                  70                  75                  80

ATC AGC TCT CTT CAA CCA GAA GAC ATT GCA ACA TAT TAT TGT CAC CAA          288
Ile Ser Ser Leu Gln Pro Glu Asp Ile Ala Thr Tyr Tyr Cys His Gln
                85                  90                  95

TAC CTC TCC TCG TGG ACG TTC GGT GGA GGG ACC AAG CTG GAG ATC AAA          336
Tyr Leu Ser Ser Trp Thr Phe Gly Gly Gly Thr Lys Leu Glu Ile Lys
            100                 105                 110

CGT                                                                      339
Arg
```

(2) INFORMATION FOR SEQ ID NO:6:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:6:

```
Asp Ile Gln Leu Thr Gln Ser Pro Ser Ser Leu Ser Ala Ser Val Gly
 1               5                   10                  15

Asp Arg Val Thr Met Ser Cys Lys Ser Ser Gln Ser Val Leu Tyr Ser
                20                  25                  30

Ala Asn His Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110

Arg
```

(2) INFORMATION FOR SEQ ID NO:7:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..348

(xi) SEQUENCE DESCRIPTION: SEQ ID NO:7:

```
CAG GTC CAG CTG GTC CAA TCA GGG GCT GAA GTC AAG AAA CCT GGG TCA          48
Gln Val Gln Leu Val Gln Ser Gly Ala Glu Val Lys Lys Pro Gly Ser
 1               5                  10                  15

TCA GTG AAG GTC TCC TGC AAG GCT TCT GGC TAC ACC TTT ACT AGC TAC          96
Ser Val Lys Val Ser Cys Lys Ala Ser Gly Tyr Thr Phe Thr Ser Tyr
                20                  25                  30

TGG CTG CAC TGG GTC AGG CAG GCA CCT GGA CAG GGT CTG GAA TGG ATT         144
Trp Leu His Trp Val Arg Gln Ala Pro Gly Gln Gly Leu Glu Trp Ile
            35                  40                  45

GGA TAC ATT AAT CCT AGG AAT GAT TAT ACT GAG TAC AAT CAG AAC TTC         192
Gly Tyr Ile Asn Pro Arg Asn Asp Tyr Thr Glu Tyr Asn Gln Asn Phe
 50                  55                  60

AAG GAC AAG GCC ACA ATA ACT GCA GAC GAA TCC ACC AAT ACA GCC TAC         240
Lys Asp Lys Ala Thr Ile Thr Ala Asp Glu Ser Thr Asn Thr Ala Tyr
 65                  70                  75                  80

ATG GAG CTG AGC AGC CTG AGG TCT GAG GAC ACG GCA TTT TAT TTT TGT         288
Met Glu Leu Ser Ser Leu Arg Ser Glu Asp Thr Ala Phe Tyr Phe Cys
                85                  90                  95

GCA AGA AGG GAT ATT ACT ACG TTC TAC TGG GGC CAA GGC ACC ACG GTC         336
Ala Arg Arg Asp Ile Thr Thr Phe Tyr Trp Gly Gln Gly Thr Thr Val
                100                 105                 110

ACC GTC TCC TCG                                                         348
Thr Val Ser Ser
        115
```

(2) INFORMATION FOR SEQ ID NO:8:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:8:

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Ser Tyr
                20                  25                  30

Trp Leu His Trp Val Arg Gln Ala Pro Gly Gln Gly Leu Glu Trp Ile
            35                  40                  45

Gly Tyr Ile Asn Pro Arg Asn Asp Tyr Thr Glu Tyr Asn Gln Asn Phe
 50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
                100                 105                 110

Thr Val Ser Ser
        115
```

(2) INFORMATION FOR SEQ ID NO:9:

(i) SEQUENCE CHARACTERISTICS:
        (A) LENGTH: 116 amino acids
        (B) TYPE: amino acid
        (D) TOPOLOGY: linear (xi) SEQUENCE DESCRIPTION: SEQ ID NO:9:

```
Gln Val Gln Leu Val Gln Gln Ser Gly Ala Glu Val Lys Lys Pro Gly Ser
```

```
1               5                   10                  15
Ser Val Lys Val Ser Cys Lys Ala Ser Gly Tyr Thr Phe Thr Ser Tyr
                20                  25                  30

Trp Leu His Trp Val Arg Gln Ala Pro Gly Gln Gly Leu Glu Trp Ile
            35                  40                  45

Gly Tyr Ile Asn Pro Arg Asn Asp Tyr Thr Glu Tyr Asn Gln Asn Phe
        50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115
```

(2) INFORMATION FOR SEQ ID NO:10:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (xi) SEQUENCE DESCRIPTION: SEQ ID NO:10:

```
TATAATCATT CCTAGGATTA ATGTATCCAA TCCATTCCAG ACCCTGTCCA GGTGCCTGCC      60

TGACCCAGTG CAGCCAGTAG CTAGTAAAGG TGTAGCCAGA AGCCTTGCAG GAGACCTTCA     120

CTGATGACCC AGGTTTCTTG ACTTCAGCC                                       149
```

(2) INFORMATION FOR SEQ ID NO:11:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO:11:

```
CCCCAGTAGA ACGTAGTAAT ATCCCTTCTT GCACAAAAAT AAAATGCCGT GTCCTCAGAC      60

CTCAGGCTGC TCAGCTCCAT GTAGGCTGTA TTGGTGGATT CGTCTGCAGT TATTGTGGCC    120

TTGTCCTTGA AGTTCTGATT                                                 140
```

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:12:

```
CCAGCTGCAG CAATCAGGGG CTGAAGTCAA GAAACCTG                              38
```

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

AAGTGGATCC TATAATCATT CCTAGGATTA ATG                                    33

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:14:

TAATCCTAGG AATGATTATA CTGAGTACAA TCAGAACTTC AAGGACCAG                   49

(2) INFORMATION FOR SEQ ID NO:15:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:15:

GGAGACGGTG ACCGTGGTGC CTTGGCCCCA GTAGAACGTA GTAA                        44

(2) INFORMATION FOR SEQ ID NO:16:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (xi) SEQUENCE DESCRIPTION: SEQ ID NO:16:

CCTAGTGGAT GCCCAGTAGA TCAGCAGTTT AGGTGCTTTC CCTGGTTTCT GCTGGTACCA       60

GGCCAAGTAG TTCTTGTGAT TTGCACTGTA TAAAACACTT TGACTGGACT TACAGCTCAT      120

AGTGACCCTA TCTCCAACAG ATGCGCTCAG                                       150

(2) INFORMATION FOR SEQ ID NO:17:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:17:

GACAAGCTTC AGCTGACCCA GTCTCCATCA TCTCTGAGCG CATCTGTTGG AG               52

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:18:

AGAGAATCGC GAAGGGACAC CAGATTCCCT AGTGGATGCC CAGTA                       45

(2) INFORMATION FOR SEQ ID NO:19:

(i) SEQUENCE CHARACTERISTICS:
        (A) LENGTH: 121 base pairs
        (B) TYPE: nucleic acid

```
            (C) STRANDEDNESS: single
            (D) TOPOLOGY: linear (xi) SEQUENCE DESCRIPTION: SEQ ID NO:19:

CCAGCTTGGT CCCTCCACCG AACGTCCACG AGGAGAGGTA TTGGTGACAA TAATATGTTG       60

CAATGTCTTC TGGTTGAAGA GAGCTGATGG TGAAAGTAAA ATCTGTCCCA GATCCGCTGC      120

C                                                                     121

(2) INFORMATION FOR SEQ ID NO:20:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:20:

GACAAGCTTT CGCGATTCTC TGGCAGCGGA TCTGGGACAG                             40

(2) INFORMATION FOR SEQ ID NO:21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:21:

GACCGGCAGA TCTGCACCTT GGTCCCTCCA CCG                                    33
```